United States Patent
Yoshioka et al.

(10) Patent No.: US 11,246,526 B2
(45) Date of Patent: Feb. 15, 2022

(54) SWALLOWING DIAGNOSIS APPARATUS AND STORAGE MEDIUM

(71) Applicants: OSAKA PREFECTURE UNIVERSITY PUBLIC CORPORATION, Sakai (JP); EuSense Medical Co., Ltd., Nishinomiya (JP); HYOGO COLLEGE OF MEDICINE, Nishinomiya (JP); J craft Co., Ltd., Izumi (JP)

(72) Inventors: Michifumi Yoshioka, Habikino (JP); Katsufumi Inoue, Sakai (JP); Yoshitaka Oku, Nishinomiya (JP)

(73) Assignees: UNIVERSITY PUBLIC CORPORATION OSAKA, Osaka (JP); EuSense Medical Co., Ltd., Nishinomiya (JP); HYOGO COLLEGE OF MEDICINE, Nishinomiya (JP); J Craft Co., Ltd., Izumi (JP)

( * ) Notice: Subject to any disclaimer, the term of this patent is extended or adjusted under 35 U.S.C. 154(b) by 301 days.

(21) Appl. No.: 16/299,405

(22) Filed: Mar. 12, 2019

(65) Prior Publication Data
US 2019/0209073 A1 Jul. 11, 2019

Related U.S. Application Data

(63) Continuation of application No. PCT/JP2017/037191, filed on Oct. 13, 2017.

(30) Foreign Application Priority Data

Oct. 14, 2016 (JP) .............................. JP2016-203157

(51) Int. Cl.
*A61B 5/00* (2006.01)
*A61B 5/08* (2006.01)
(Continued)

(52) U.S. Cl.
CPC .............. *A61B 5/4205* (2013.01); *A61B 5/08* (2013.01); *A61B 5/0816* (2013.01);
(Continued)

(58) Field of Classification Search
CPC ............ A61B 10/00; A61B 2562/0204; A61B 2562/0247; A61B 5/08; A61B 5/0816;
(Continued)

(56) References Cited

U.S. PATENT DOCUMENTS

2008/0269646 A1 10/2008 Chau et al.
2012/0150073 A1 6/2012 Dunn et al.
(Continued)

FOREIGN PATENT DOCUMENTS

CN 102339607 A 2/2012
CN 103646649 A 3/2014
(Continued)

OTHER PUBLICATIONS

Schapire; Rob "Machine Learning Algorithms for Classification" Princeton University. Accessed on waybackmachine Apr. 5, 2021 @ https://www.cs.princeton.edu/~schapire/talks/picasso-minicourse.pdf Saved Jun. 27, 2013 (Year: 2013).*
(Continued)

*Primary Examiner* — Sean P Dougherty
*Assistant Examiner* — Alexander H Connor
(74) *Attorney, Agent, or Firm* — Westerman, Hattori, Daniels & Adrian, LLP

(57) ABSTRACT

A swallowing diagnosis apparatus includes a controller which enables a first swallowing determination process of determining whether or not there is an aspiration risk in the swallowing on the basis of respiratory phases before and after a period in which swallowing has been estimated as having occurred; and a second swallowing determination process of extracting reference information including at least
(Continued)

one of the sound information and the respiration information in a predetermined period including the period in which swallowing has been estimated as having occurred, obtaining a feature quantity from the extracted reference information, and performing a machine learning process on the obtained feature quantity to determine whether or not there is a possibility of dysphagia in the swallowing; and a display control process of causing a determination result obtained by the first swallowing determination process and a determination result obtained by the second swallowing determination process to be displayed.

15 Claims, 25 Drawing Sheets

(51) Int. Cl.
  *G06N 20/10*    (2019.01)
  *A61B 5/11*     (2006.01)
  *A61B 7/00*     (2006.01)

(52) U.S. Cl.
  CPC .............. *A61B 5/0826* (2013.01); *A61B 5/11* (2013.01); *A61B 5/1107* (2013.01); *A61B 5/7257* (2013.01); *A61B 5/7275* (2013.01); *A61B 7/003* (2013.01); *A61B 7/008* (2013.01); *G06N 20/10* (2019.01)

(58) Field of Classification Search
  CPC ....... A61B 5/0826; A61B 5/11; A61B 5/1107; A61B 5/4205; A61B 5/7257; A61B 5/726; A61B 5/7264; A61B 5/7267; A61B 5/7275; A61B 7/003; A61B 7/008; G06N 20/10; G16H 50/30; G16H 50/70
  See application file for complete search history.

(56) References Cited

U.S. PATENT DOCUMENTS

| | | | |
|---|---|---|---|
| 2014/0188006 A1 | 7/2014 | Alshaer et al. | |
| 2016/0026767 A1* | 1/2016 | Sarrafzadeh | A61B 7/008 600/586 |
| 2016/0143575 A1* | 5/2016 | Oku | A61B 7/003 600/529 |
| 2016/0242695 A1 | 8/2016 | Ajima | |

FOREIGN PATENT DOCUMENTS

| | | |
|---|---|---|
| CN | 105658142 A | 6/2016 |
| JP | 2008-502386 A | 1/2008 |
| JP | 2016-34325 A | 3/2016 |
| WO | 2014/203433 A1 | 12/2014 |
| WO | 2015/029501 A1 | 3/2015 |

OTHER PUBLICATIONS

New Hampshire Bureau of Developmental Disabilities "Dysphagia and Aspiration" Accessed on waybackmachine Apr. 5, 2021 @ https://web.archive.org/web/20150922234251/https://www.dhhs.nh.gov/dcbcs/bds/nurses/documents/dysphagiaaspiration.pdf Saved Sep. 22, 2015 (Year: 2015).*

Written Opinion dated Jan. 23, 2020, issued in counterpart SG application No. 11201902898W. (6 pages).

International Search Report dated Jan. 9, 2018, issued in counterpart application No. PCT/JP2017/037191, w/ English translation (3 pages).

Notification of Transmittal of Translation of the International Preliminary Report on Patentability (Form PCT/IB/338) issued in counterpart International Application No. PCT/JP2017/037191 dated Apr. 18, 2019, with Forms PCT/IPEA/416 and PCT/IPEA/409; with English translation. (12 pages).

Shirazi, Samaneh Sarraf, "Acoustical Analysis of the swallowing Mechanism for Diagnosis of Dysphagia", Department of Biomedical Engineering University of Manitoba, Winnipeg, Manitoba, Canada, Jun. 1, 2014, pp. 1-135; Cited in Extended European Search Report dated Nov. 13, 2020. (134 pages).

Extended (Supplementary Partial) European Search Report dated Nov. 13, 2020, issued in counterpart EP Application No. 17860831.1. (15 pages).

Office Action dated Apr. 26, 2021, issued in counterpart CN Application No. 201780058289.4 with English translation. (22 pages).

Office Action dated Dec. 1, 2021, issued in counterpart CN application No. 201780058289.4, with English translation. (26 pages).

* cited by examiner

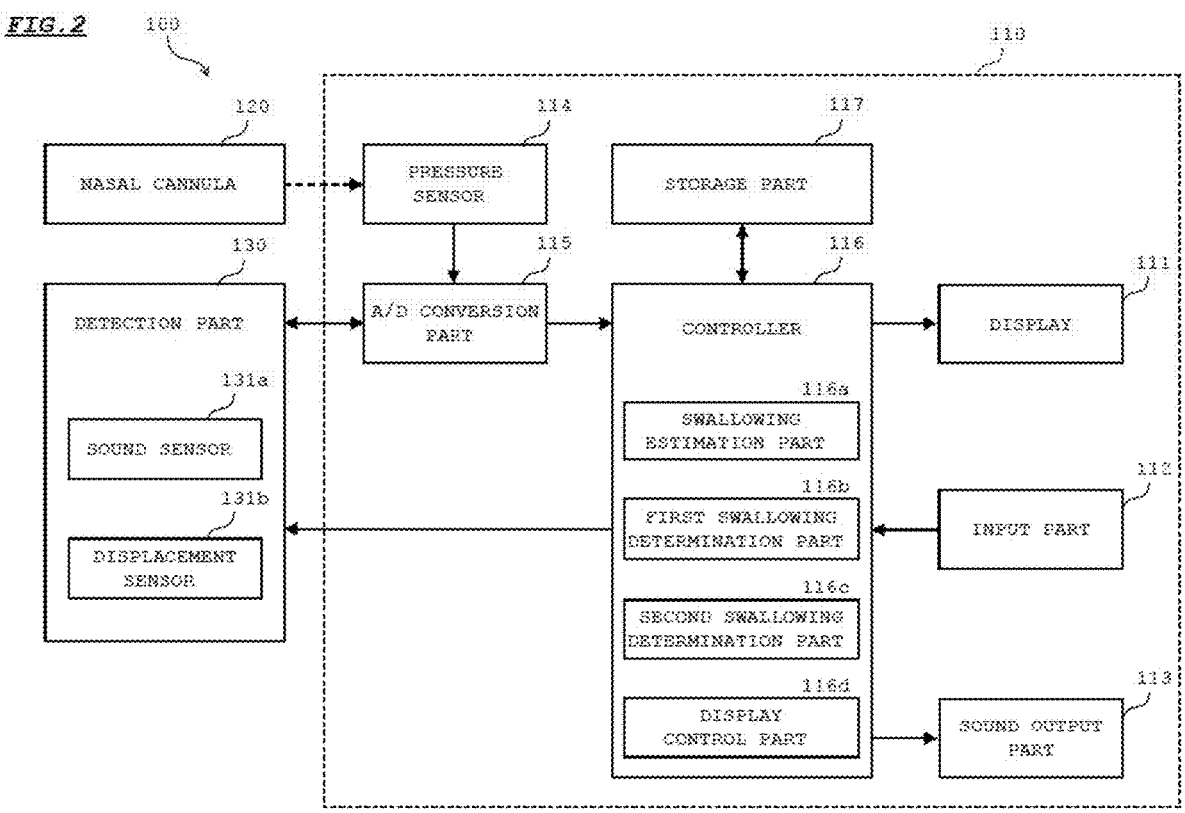

RESPIRATORY PRESSURE DATA

BIOGENIC SOUND DATA

LARYNX DISPLACEMENT DATA

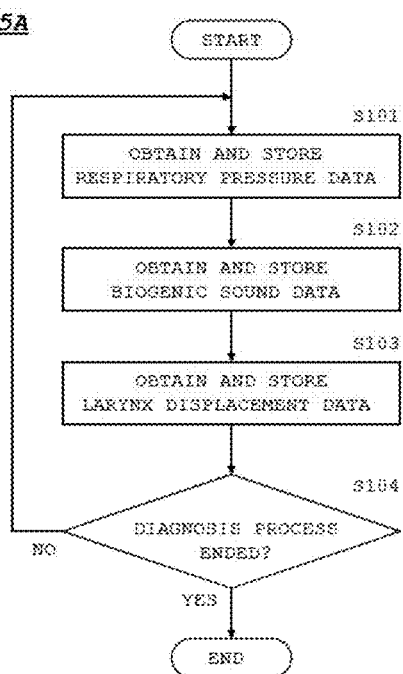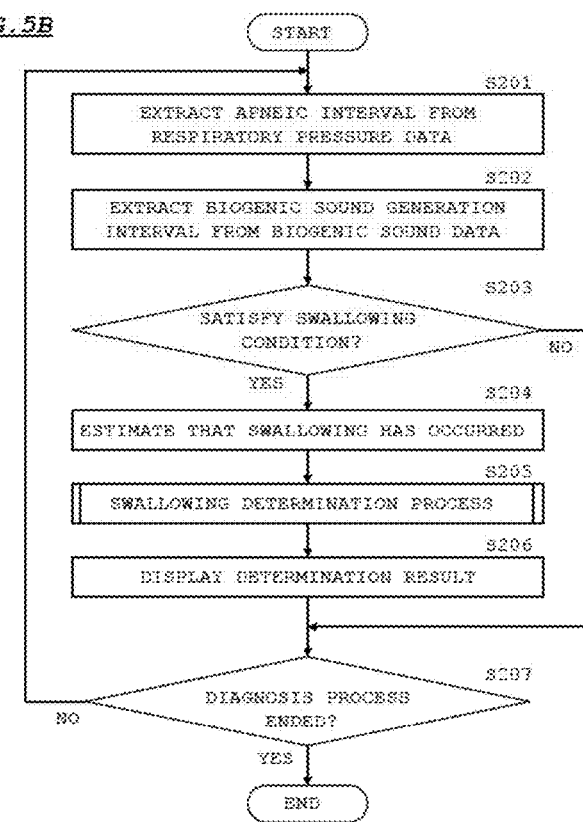

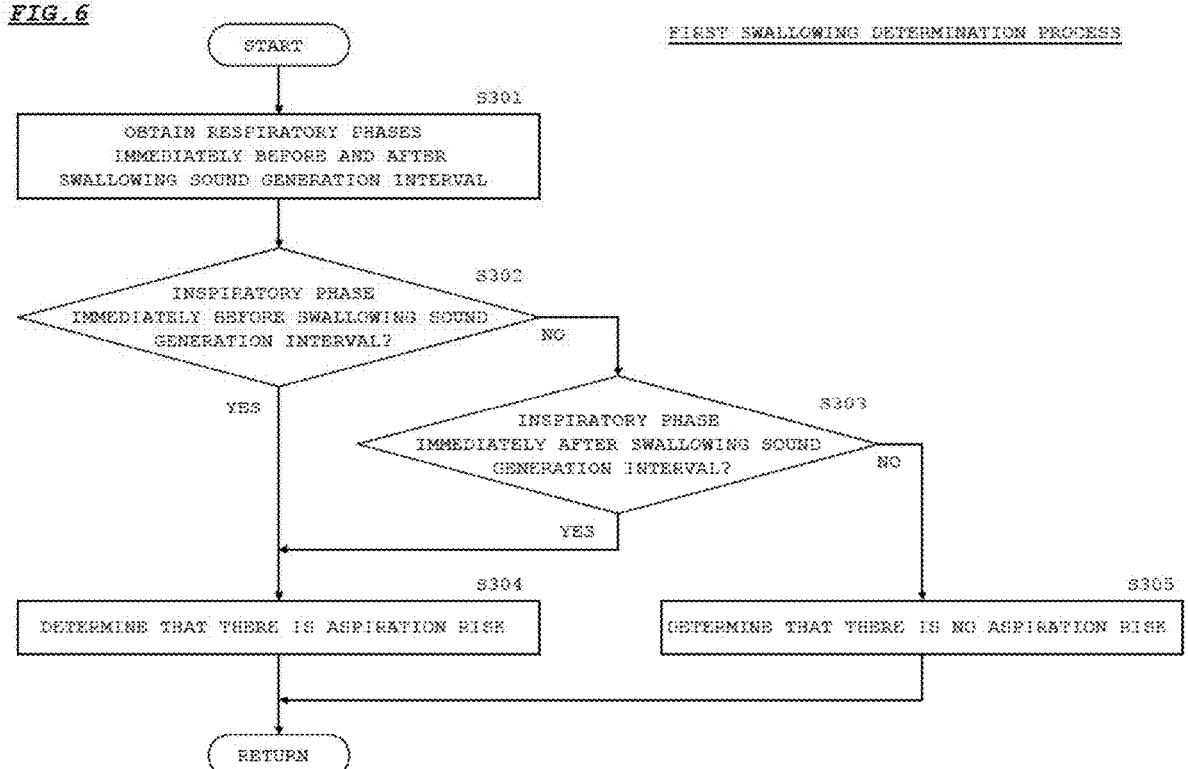

FIG. 9A
LPC ORDER : 8
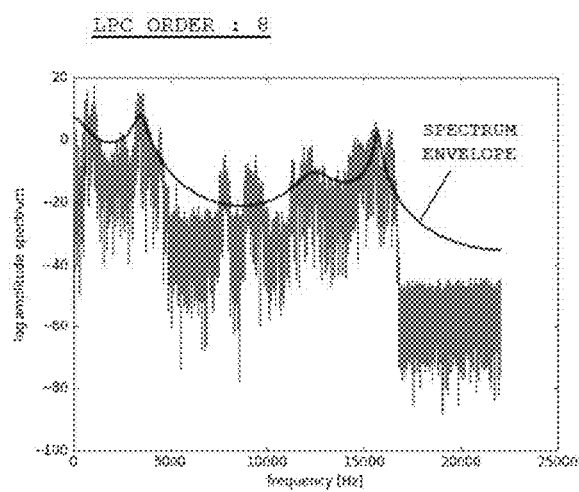
FIG. 9B                  <EXAMINATION 1>
LPC ORDER : 16
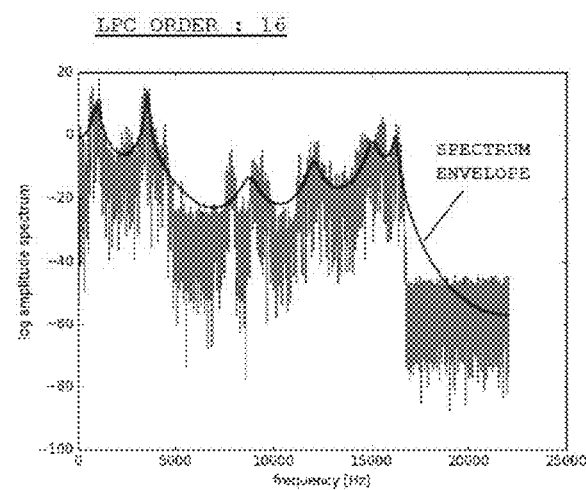

FIG. 10A

RESULT OF LARYNX DISPLACEMENT DATA
(NUMBER OF GROUPS: 10)   <LPC SPECTRUM>

| ENTIRETY: 76.4% (LPC ORDER: 32) | | CORRECT LABEL | |
|---|---|---|---|
| | | HEALTHY SUBJECT | PATIENT |
| DETERMINATION LABEL | HEALTHY SUBJECT | 82.5% | 34.4% |
| | PATIENT | 17.5% | 65.6% |

FIG. 10B

RESULT OF RESPIRATORY PRESSURE DATA
(NUMBER OF GROUPS: 10)   <LPC SPECTRUM>

| ENTIRETY: 87.6% (LPC ORDER: 32) | | CORRECT LABEL | |
|---|---|---|---|
| | | HEALTHY SUBJECT | PATIENT |
| DETERMINATION LABEL | HEALTHY SUBJECT | 96.5% | 28.1% |
| | PATIENT | 3.5% | 71.9% |

FIG. 10C

RESULT OF BIOGENIC SOUND DATA
(NUMBER OF GROUPS: 10)   <LPC SPECTRUM>

| ENTIRETY: 79.2% (LPC ORDER: 32) | | CORRECT LABEL | |
|---|---|---|---|
| | | HEALTHY SUBJECT | PATIENT |
| DETERMINATION LABEL | HEALTHY SUBJECT | 89.5% | 39.1% |
| | PATIENT | 10.5% | 60.9% |

FIG.11A  RESULT OF LARYNX DISPLACEMENT DATA
(NUMBER OF GROUPS: 10)                                  <LPC COEFFICIENT>

| ENTIRETY: 69.7% | | CORRECT LABEL | |
|---|---|---|---|
| (LPC ORDER: 16) | | HEALTHY SUBJECT | PATIENT |
| DETERMINATION LABEL | HEALTHY SUBJECT | 76.3% | 42.2% |
| | PATIENT | 23.7% | 57.8% |

FIG.11B  RESULT OF RESPIRATORY PRESSURE DATA
(NUMBER OF GROUPS: 10)                                  <LPC COEFFICIENT>

| ENTIRETY: 88.8% | | CORRECT LABEL | |
|---|---|---|---|
| (LPC ORDER: 32) | | HEALTHY SUBJECT | PATIENT |
| DETERMINATION LABEL | HEALTHY SUBJECT | 93.9% | 20.3% |
| | PATIENT | 6.1% | 79.7% |

FIG.11C  RESULT OF BIOGENIC SOUND DATA
(NUMBER OF GROUPS: 10)                                  <LPC COEFFICIENT>

| ENTIRETY: 77.5% | | CORRECT LABEL | |
|---|---|---|---|
| (LPC ORDER: 8) | | HEALTHY SUBJECT | PATIENT |
| DETERMINATION LABEL | HEALTHY SUBJECT | 88.6% | 42.2% |
| | PATIENT | 11.4% | 57.8% |

FIG. 12A RESULT OF LARYNX DISPLACEMENT DATA
(NUMBER OF GROUPS: 10) <MFCC>

| ENTIRETY: 69.7% | | CORRECT LABEL | |
|---|---|---|---|
| | | HEALTHY SUBJECT | PATIENT |
| DETERMINATION LABEL | HEALTHY SUBJECT | 74.6% | 39.1% |
| | PATIENT | 25.4% | 60.9% |

FIG. 12B RESULT OF RESPIRATORY PRESSURE DATA
(NUMBER OF GROUPS: 10) <MFCC>

| ENTIRETY: 86.5% | | CORRECT LABEL | |
|---|---|---|---|
| | | HEALTHY SUBJECT | PATIENT |
| DETERMINATION LABEL | HEALTHY SUBJECT | 94.7% | 28.1% |
| | PATIENT | 5.3% | 71.9% |

FIG. 12C RESULT OF BIOGENIC SOUND DATA
(NUMBER OF GROUPS: 10) <MFCC>

| ENTIRETY: 69.7% | | CORRECT LABEL | |
|---|---|---|---|
| | | HEALTHY SUBJECT | PATIENT |
| DETERMINATION LABEL | HEALTHY SUBJECT | 77.2% | 43.7% |
| | PATIENT | 22.8% | 56.3% |

FIG. 13A  <LARYNX DISPLACEMENT>

| FEATURE QUANTITY | ACCURACY | HEALTHY SUBJECT DETERMINATION ACCURACY | PATIENT DETERMINATION ACCURACY |
|---|---|---|---|
| LPC SPECTRUM | 76.4% | 82.5% | 65.6% |
| LPC COEFFICIENT | 69.7% | 76.3% | 57.8% |
| MFCC | 69.7% | 74.6% | 60.9% |

FIG. 13B  <RESPIRATORY PRESSURE>

| FEATURE QUANTITY | ACCURACY | HEALTHY SUBJECT DETERMINATION ACCURACY | PATIENT DETERMINATION ACCURACY |
|---|---|---|---|
| LPC SPECTRUM | 87.6% | 96.5% | 71.9% |
| LPC COEFFICIENT | 88.8% | 93.9% | 79.7% |
| MFCC | 86.5% | 94.7% | 71.9% |

FIG. 13C  <BIOGENIC SOUND>

| FEATURE QUANTITY | ACCURACY | HEALTHY SUBJECT DETERMINATION ACCURACY | PATIENT DETERMINATION ACCURACY |
|---|---|---|---|
| LPC SPECTRUM | 79.2% | 89.5% | 60.9% |
| LPC COEFFICIENT | 77.5% | 88.6% | 57.8% |
| MFCC | 69.7% | 77.2% | 56.3% |

*FIG.14*                                                             <EXAMINATION 2>

<LPC SPECTRUM/NON-TIME SERIES>

| LPC ORDER | DATA | F VALUE | ACCURACY [%] | HEALTHY SUBJECT DETERMINATION ACCURACY [%] | PATIENT DETERMINATION ACCURACY [%] |
|---|---|---|---|---|---|
| 8 | ESPIRATORY PRESSURE | 45.9 | 75.1 | 89.2 | 38.2 |
|  | LARYNX DISPLACEMENT | 50.1 | 72.8 | 81.7 | 49.5 |
|  | BIOGENIC SOUND | 55.7 | 76.2 | 84.5 | 54.2 |
| 16 | ESPIRATORY PRESSURE | 41.9 | 77.2 | 95.3 | 29.7 |
|  | LARYNX DISPLACEMENT | 46.1 | 72.0 | 82.9 | 43.4 |
|  | BIOGENIC SOUND | 62.4 | 79.4 | 86.2 | 61.8 |
| 32 | ESPIRATORY PRESSURE | 44 | 72.1 | 84.5 | 39.6 |
|  | LARYNX DISPLACEMENT | 50.1 | 73.8 | 83.8 | 47.6 |
|  | BIOGENIC SOUND | 61.7 | 80.7 | 90.1 | 56.1 |

*FIG.15*

<LPC SPECTRUM/TIME SERIES>

| LPC ORDER | DATA | F VALUE | ACCURACY [%] | HEALTHY SUBJECT DETERMINATION ACCURACY [%] | PATIENT DETERMINATION ACCURACY [%] |
|---|---|---|---|---|---|
| 8 | ESPIRATORY PRESSURE | 53.0 | 75.3 | 84.7 | 50.5 |
| | LARYNX DISPLACEMENT | 51.3 | 73.6 | 82.4 | 50.5 |
| | BIOGENIC SOUND | 55.3 | 76.0 | 84.5 | 53.8 |
| 16 | ESPIRATORY PRESSURE | 50.0 | 73.7 | 83.6 | 47.6 |
| | LARYNX DISPLACEMENT | 47.2 | 72.0 | 82.2 | 45.3 |
| | BIOGENIC SOUND | 56.8 | 78.6 | 89.2 | 50.9 |
| 32 | ESPIRATORY PRESSURE | 47.6 | 75.4 | 88.7 | 40.6 |
| | LARYNX DISPLACEMENT | 45.5 | 72.3 | 83.8 | 42.0 |
| | BIOGENIC SOUND | 64.1 | 80.6 | 87.4 | 62.7 |

FIG. 20A

<LPC SPECTRUM>

| PRESENCE OR ABSENCE OF TIME SERIES | F VALUE | ACCURACY [%] | HEALTHY SUBJECT DETERMINATION ACCURACY [%] | PATIENT DETERMINATION ACCURACY [%] |
|---|---|---|---|---|
| WITHOUT TIME SERIES | 62.4 | 79.4 | 86.2 | 61.8 |
| WITH TIME SERIES | 64.1 | 80.6 | 87.4 | 62.7 |

FIG. 20B

<EXAMINATION 3>

COMBINATION OF 3 DATA      <LPC SPECTRUM>

| PRESENCE OR ABSENCE OF TIME SERIES | F VALUE | ACCURACY [%] | HEALTHY SUBJECT DETERMINATION ACCURACY [%] | PATIENT DETERMINATION ACCURACY [%] |
|---|---|---|---|---|
| 8 | 70.8 | 85.2 | 92.8 | 65.1 |
| 16 | 71.2 | 85.2 | 92.3 | 66.5 |
| 32 | 73.7 | 86.6 | 93.7 | 67.9 |

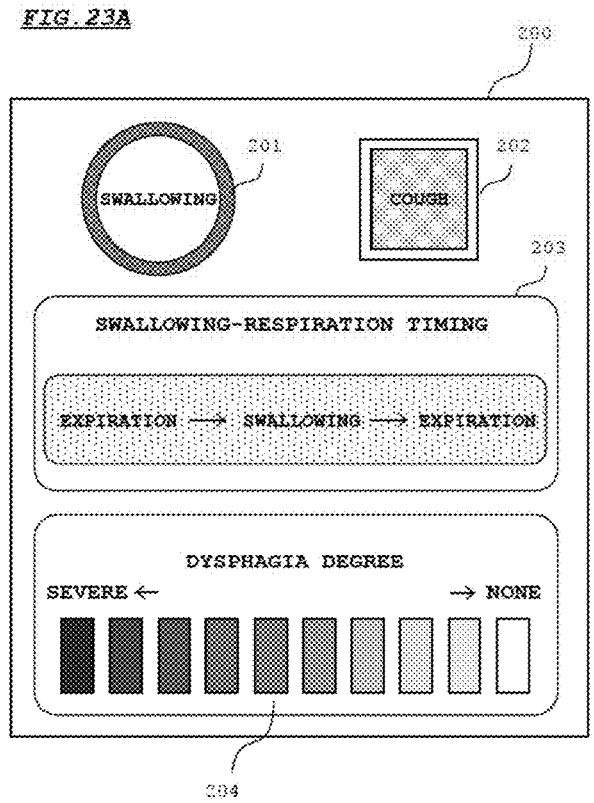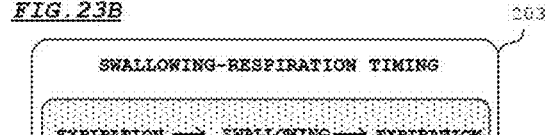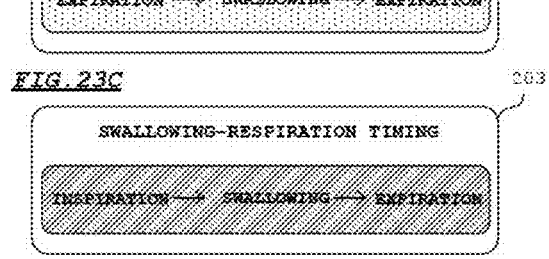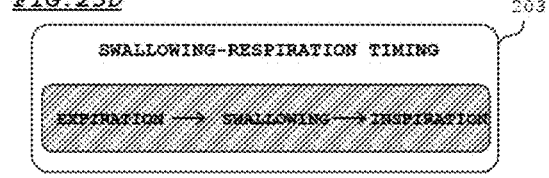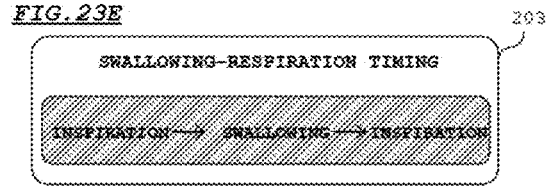

SWALLOWING DIAGNOSIS APPARATUS AND STORAGE MEDIUM

CROSS REFERENCE TO RELATED APPLICATION

This application is a continuation of International Application No. PCT/JP2017/037191 filed on Oct. 13, 2017, entitled "DEGLUTITION DIAGNOSIS DEVICE AND PROGRAM", which claims priority under 35 U.S.C. Section 119 of Japanese Patent Application No. 2016-203157 filed on Oct. 14, 2016, entitled "SWALLOWING DIAGNOSIS DEVICE AND PROGRAM". The disclosure of the above applications is incorporated herein by reference.

BACKGROUND OF THE INVENTION

1. Field of the Invention

The present invention relates to a swallowing diagnosis apparatus for diagnosing a risk of aspiration, and relates to a storage medium having stored therein a program for providing a function of swallowing diagnosis to a computer.

2. Disclosure of Related Art

Aspiration pneumonias caused by aspiration are serious problems, particularly for elderly persons. "Aspiration" is a pathological condition in which swallowing cannot be appropriately performed and the thing having taken in enters not the esophagus but the trachea. At present, there is a desire for development of swallowing diagnosis apparatuses that can appropriately diagnose a risk of aspiration.

Japanese National Phase PCT Laid-Open Publication No. 2008-502386 describes a system in which: features are extracted from an acceleration signal with respect to the pharynx; and, on the basis of the extracted features, swallowing activities (swallowing, aspiration, and the like) are classified by a radial basis function neural network. In the system, stationarity, normality, and dispersion ratio are used as the features extracted from the acceleration signal. As for the classified swallowing activities, swallowing and aspiration are indicated in different colors.

Aspiration could occur as a result of characteristics (habit, etc.) of an individual being modified due to the age or diseases. Meanwhile, even when an individual does not have such characteristics, aspiration could occur due to dysphagia caused by diseases and the like. Therefore, it is desirable to comprehensively determine the risk of aspiration in a patient on the basis of these aspects.

SUMMARY OF THE INVENTION

A first mode of the present invention relates to a swallowing diagnosis apparatus. A swallowing diagnosis apparatus according to this mode includes: a sound detection part configured to detect sound of a larynx portion; a respiration detection part configured to detect respiration; and a controller. The controller is configured to perform: a swallowing estimation process of estimating that swallowing has occurred, on the basis of matching realized between a biogenic sound generation interval for which a feature quantity satisfying a swallowing estimation condition has been obtained in sound information outputted from the sound detection part, and an apneic interval for which respiration has not been detected for longer than or equal to a predetermined time in respiration information outputted from the respiration detection part; a first swallowing determination process of detecting, from the respiration information, respiratory phases before and after a period in which swallowing has been estimated as having occurred by the swallowing estimation process, and determining whether or not there is an aspiration risk in the swallowing on the basis of the detected respiratory phases; a second swallowing determination process of extracting reference information including at least one of the sound information and the respiration information in a predetermined period including the period in which swallowing has been estimated as having occurred by the swallowing estimation process, obtaining a feature quantity from the extracted reference information, and performing a machine learning process on the obtained feature quantity to determine whether or not there is a possibility of dysphagia in the swallowing; and a display control process of causing a display to display, in a contrastable manner, a determination result obtained by the first swallowing determination process and a determination result obtained by the second swallowing determination process with respect to an identical period in which swallowing has been estimated as having occurred by the swallowing estimation process.

A second mode of the present invention relates to a swallowing diagnosis apparatus. A swallowing diagnosis apparatus according to this mode includes: a sound detection part configured to detect sound of a larynx portion; a respiration detection part configured to detect respiration; and a controller. The controller is configured to perform: a swallowing estimation process of estimating that swallowing has occurred, on the basis of matching realized between a biogenic sound generation interval for which a feature quantity satisfying a swallowing estimation condition has been obtained in sound information outputted from the sound detection part, and an apneic interval for which respiration has not been detected for longer than or equal to a predetermined time in respiration information outputted from the respiration detection part; and a swallowing determination process of extracting reference information including at least one of the sound information and the respiration information in a predetermined period including a period in which swallowing has been estimated as having occurred by the swallowing estimation process, subjecting the extracted reference information to Fourier transform to obtain a frequency spectrum, applying linear predictive coding to the obtained frequency spectrum to obtain a spectrum envelope, sampling the obtained spectrum envelope at a predetermined frequency interval to obtain a feature quantity, and performing a machine learning process on the obtained feature quantity to determine whether or not there is a possibility of dysphagia in the swallowing.

A third mode of the present invention is a storage medium having stored therein a program configured to provide a computer with the functions of the swallowing estimation process, the first swallowing determination process, the second swallowing determination process, and the display control process according to the first mode.

BRIEF DESCRIPTION OF THE DRAWINGS

The above and other objects and new features of the present invention will be fully clarified by the following description of the embodiment, when read in conjunction with accompanying drawings.

FIG. 2 is a block diagram showing a configuration of the swallowing diagnosis apparatus according to the embodiment;

FIG. 5A is a flow chart showing a process of obtaining various types of data in the swallowing diagnosis apparatus according to the embodiment;

FIG. 5B is a flow chart showing a swallowing diagnosis process performed in the swallowing diagnosis apparatus according to the embodiment;

FIG. 6 is a flow chart showing a first swallowing determination process performed in the swallowing diagnosis apparatus according to the embodiment;

FIGS. 9A and 9B are each a diagram showing a method for obtaining a parameter value based on an LPC spectrum in Examination 1 according to the embodiment;

FIGS. 10A to 10C are each a diagram showing examination results obtained when the LPC spectrum was used as a feature parameter in Examination 1 according to the embodiment;

FIGS. 11A to 11C are each a diagram showing examination results obtained when the coefficient at an LPC order was used as the feature parameter in Examination 1 according to the embodiment;

FIGS. 12A to 12C are each a diagram showing examination results obtained when MFCC was used as the feature parameter in Examination 1 according to the embodiment;

FIGS. 13A to 13C are each a diagram summarizing the examination results of Examination 1 according to the type of data (larynx displacement, respiratory pressure, swallowing sound), according to the embodiment;

FIG. 14 is a diagram showing, by numerical values, the examination results obtained when the feature parameter value was obtained on the basis of the LPC spectrum according to a non-time-series method in Examination 2 according to the embodiment;

FIG. 15 is a diagram showing, by numerical values, the examination results obtained when the feature parameter value was obtained on the basis of the LPC spectrum according to a time-series method in Examination 2 according to the embodiment;

FIG. 20A is a diagram summarizing, in a table, the examination results of Examination 2 according to the embodiment;

FIG. 20B is a diagram summarizing, in a table, the examination results of Examination 3 according to the embodiment;

FIG. 23A is a diagram showing a configuration of a screen for displaying a diagnosis result of the swallowing diagnosis apparatus according to the embodiment;

FIGS. 23B to 23E are each a diagram showing a display form for a first determination result according to the embodiment;

It should be noted that the drawings are solely for description and do not limit the scope of the present invention by any degree.

DESCRIPTION OF THE PREFERRED EMBODIMENTS

Figure 1:
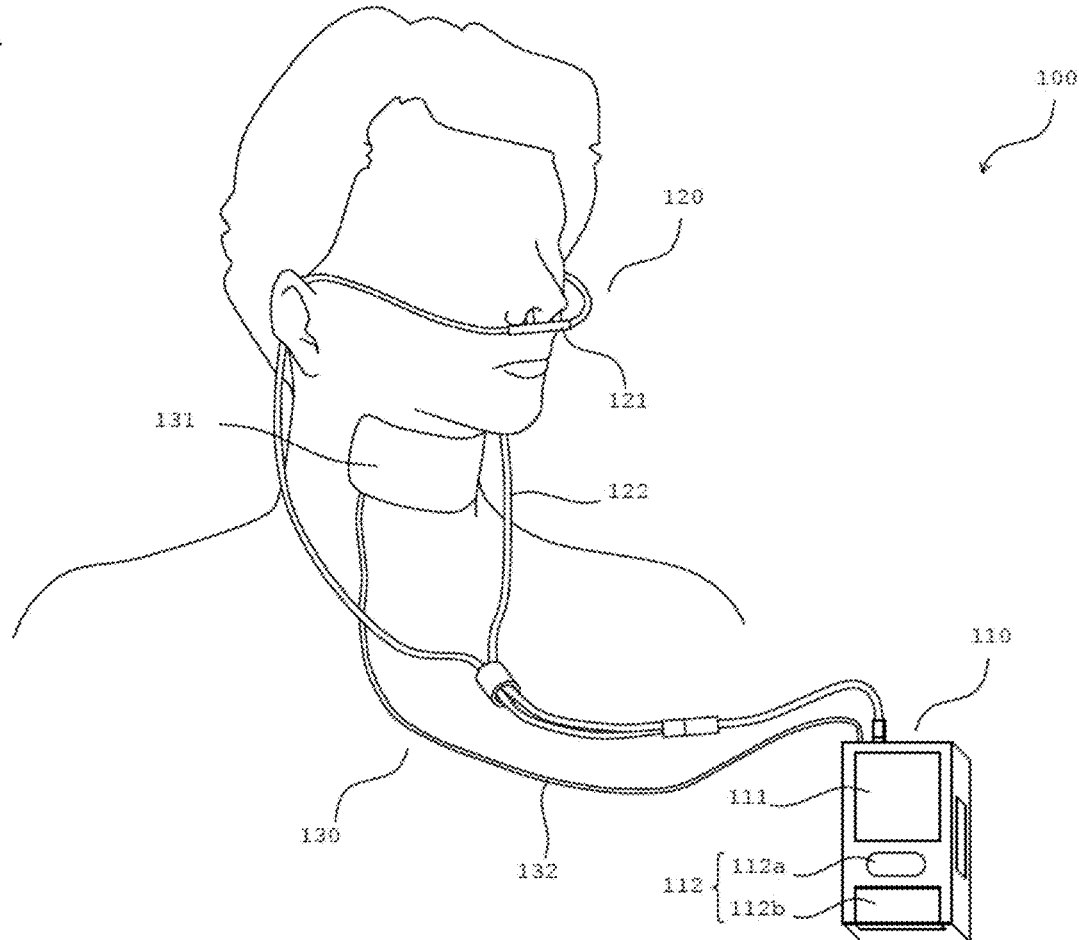
FIG. 1 is an external view showing a configuration of a swallowing diagnosis apparatus according to an embodiment.

FIG. 1 is an external view showing a swallowing diagnosis apparatus 100 according to the present embodiment.

The swallowing diagnosis apparatus 100 includes a terminal device 110, a nasal cannula 120, and a detection part 130.

The terminal device 110 includes a display 111 and an input part 112. The terminal device 110 is configured to be small and light in weight so as to be easily carried by a patient. The display 111 is implemented by a color liquid-crystal monitor. The input part 112 includes a button 112a for starting and ending a swallowing diagnosis. Further, the input part 112 includes a group of keys, which are used for setting operation while a cover 112b is open.

The nasal cannula 120 includes: an attachment part 121 having a pair of tubular members; and a tube 122 connected to both ends of the attachment part 121. The pair of tubular members of the attachment part 121 are inserted into the nasal cavities of the patient, and the other end of the tube 122 is connected to the terminal device 110. Accordingly, when the patient performs respiration, the air in the tube 122 flows, and the flow of the air in the tube 122 is detected as a pressure by a pressure sensor 114 (see FIG. 2) in the terminal device 110. Even when the patient is breathing through the mouth, since the nasal cavities and the oral cavity are connected to each other, the air in the tube 122 flows and the pressure changes.

The detection part 130 includes a pad 131 which is thin and flexible; and a cable 132. The pad 131 is attached to a larynx portion of the patient. The pad 131 includes: a sound sensor 131a (see FIG. 2) for detecting sound of the larynx portion; and a displacement sensor 131b (see FIG. 2) for detecting, in terms of pressure, a displacement of the hyoid bone in accordance with deformation of the larynx portion. The other end of the cable 132 is connected to the terminal device 110.

The nasal cannula 120 and the pressure sensor 114 constitute a respiration detection part. The sound sensor 131a constitutes a sound detection part. The displacement sensor 131b constitutes a displacement detection part. A pressure signal outputted from the pressure sensor 114, a sound signal outputted from the sound sensor 131a, and a displacement signal outputted from the displacement sensor 131b are examples of respiration information, sound information, and displacement information, respectively.

FIG. 2 is a block diagram showing a configuration of the swallowing diagnosis apparatus 100.

The terminal device 110 includes: a sound output part 113, the pressure sensor 114, an A/D conversion part 115, a controller 116, and a storage part 117, in addition to the display 111 and the input part 112 shown in FIG. 1.

The sound output part 113 includes a buzzer and a speaker, and outputs to outside a predetermined sound on the basis of control by the controller 116.

The pressure sensor 114 detects, as a pressure, the flow of air guided by the tube 122 of the nasal cannula 120, and outputs the detected analog pressure signal to the A/D conversion part 115. The detection part 130 includes the sound sensor 131a and the displacement sensor 131b. The sound sensor 131a detects sound in the vicinity of the larynx portion of the patient, and outputs the detected analog sound signal to the A/D conversion part 115. The displacement sensor 131b detects, as a displacement of the hyoid bone, deformation of the larynx portion of the patient, and outputs the detected analog displacement signal to the A/D conversion part 115.

The A/D conversion part 115 samples, in a predetermined cycle, the pressure signal, the sound signal, and the displacement signal respectively outputted from the pressure sensor 114, the sound sensor 131a, and the displacement sensor 131b, and outputs pieces of digital data that correspond to the respective sampled signals, to the controller 116.

Hereinafter, the respective pieces of digital data obtained through A/D conversion of the pressure signal, the sound signal, and the displacement signal will be referred to as respiratory pressure data, biogenic sound data, and larynx displacement data.

The controller 116 includes an arithmetic processing circuit such as a CPU (Central Processing Unit), and controls components of the terminal device 110 in accordance with a program stored in the storage part 117. The storage part 117 includes a storage medium such as a ROM (Read Only Memory), a RAM (Random Access Memory), or the like, and stores therein a program to be executed by the controller 116. The storage part 117 is used as a work area for processing performed by the controller 116.

The controller 116 is provided with functions of a swallowing estimation part 116a, a first swallowing determination part 116b, a second swallowing determination part 116c, and a display control part 116d, by the program stored in the storage part 117. This program may be installed in the storage part 117 in advance, or may be downloaded to the storage part 117 from an attachable/detachable memory medium or a communication network.

The swallowing estimation part 116a estimates that a swallowing has been performed by the patient, on the basis of respiratory pressure data, biogenic sound data, and larynx displacement data inputted from the A/D conversion part 115. The swallowing estimation method performed in the swallowing estimation part 116a will be described later with reference to FIGS. 3A to 3C, and FIGS. 4A to 4D.

With respect to the swallowing estimated by the swallowing estimation part 116a, the first swallowing determination part 116b determines whether or not there is a risk of aspiration. This determination is performed on the basis of the respiratory pressure data inputted from the A/D conversion part 115. The swallowing risk determination method performed in the first swallowing determination part 116b will be described later with reference to FIG. 6.

With respect to the swallowing estimated by the swallowing estimation part 116a, the second swallowing determination part 116c determines whether or not there is a possibility of dysphagia. This determination is performed on the basis of at least one of the respiratory pressure data, the biogenic sound data, and the larynx displacement data inputted from the A/D conversion part 115. In the present embodiment, the determination in the second swallowing determination part 116c is performed, using all of the respiratory pressure data, the biogenic sound data, and the larynx displacement data. The dysphagia possibility determination method performed in the second swallowing determination part 116c will be described later with reference to FIG. 7 and FIG. 8.

The display control part 116d performs a process of: configuring a screen including determination results obtained in the first swallowing determination part 116b and the second swallowing determination part 116c; and causing the display 111 to display the screen. The screen configured by the display control part 116d will be described later with reference to FIGS. 23A and 23B.

<Swallowing Estimation Method>

Next, with reference to FIGS. 3A to 3C and FIGS. 4A to 4D, the swallowing estimation method performed in the swallowing estimation part 116a is described.

Figure 3A:
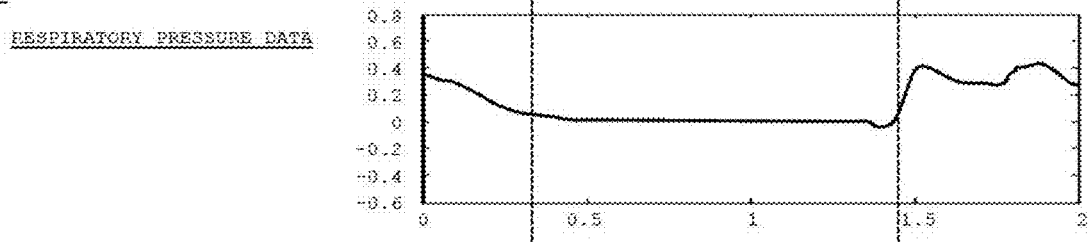
FIGS. 3A to 3C are diagrams respectively showing examples of respiratory pressure data, biogenic sound data, and larynx displacement data according to the embodiment.
Figure 3B:
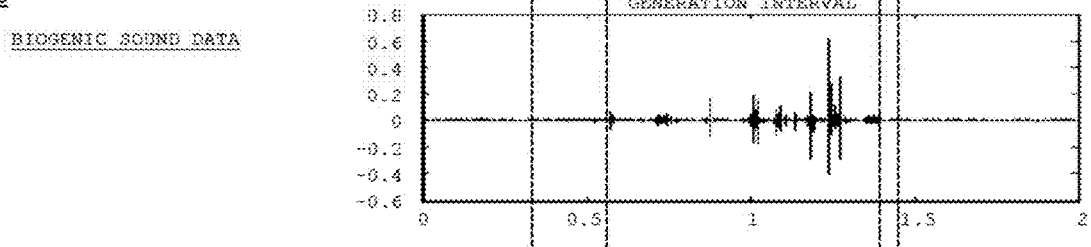
Figure 3C:
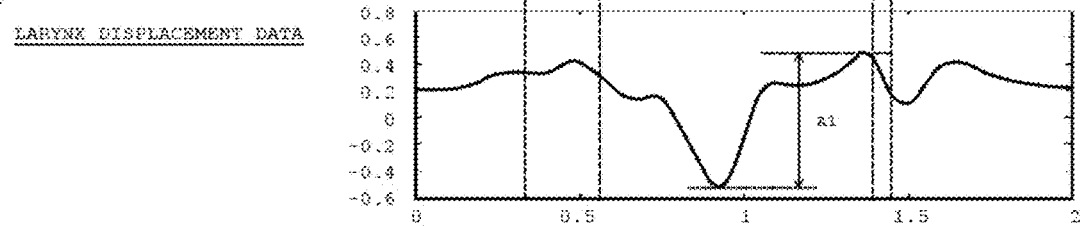

FIGS. 3A to 3C are diagrams respectively showing examples of respiratory pressure data, biogenic sound data, and larynx displacement data. In FIGS. 3A to 3C, biogenic sound data, respiratory pressure data, and larynx displacement data obtained in the same period and yet to be subjected to A/D conversion are shown in the form of analog signal waveforms. The horizontal axis represents time (second), and the vertical axis represents intensity after normalization.

Figure 4A:
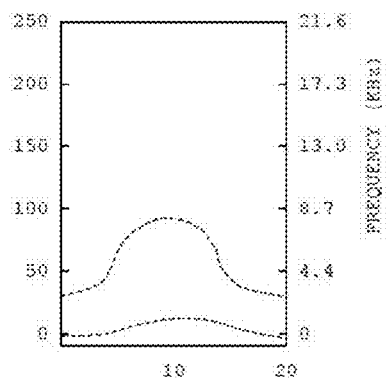
FIG. 4A is a schematic diagram showing a spectrogram according to the embodiment.

The swallowing estimation part 116a creates a spectrogram by performing short-time Fourier transform on the biogenic sound data, and extracts biogenic sound generation intervals on the basis of the created spectrogram. Specifically, with respect to the biogenic sound data of the entire interval, the swallowing estimation part 116a sets the window function (sampling range) to 1.5 seconds to cut out biogenic sound data, and performs short-time Fourier transform on the cut-out biogenic sound data to create a spectrogram as shown in FIG. 4A. That is, the swallowing estimation part 116a performs Fourier transform in a unit time (time width: 1.5 seconds), and this is sequentially performed with 0.2 seconds shifted every time, whereby a spectrogram is created. The example shown in FIG. 4A is a spectrogram created for 20 unit-time widths, that is, for 4 seconds.

The swallowing estimation part 116a obtains the total sum of the amplitudes of the created spectrogram to perform conversion into signal intensity data, and extracts, as a biogenic sound generation interval, each interval that has a value exceeding the noise average+2SD (standard deviation). Accordingly, with respect to the biogenic sound data of the entire interval, biogenic sound generation intervals are specified. FIGS. 3B and 3C additionally show a biogenic sound generation interval extracted in this manner.

Next, with respect to the respiratory pressure data, the swallowing estimation part 116a extracts, as an apneic interval, each interval that has a value less than or equal to a threshold that is set in consideration of noise. Accordingly, with respect to the respiratory pressure data of the entire interval, apneic intervals are set. FIG. 3A additionally shows an apneic interval extracted in this manner.

Figure 4B:
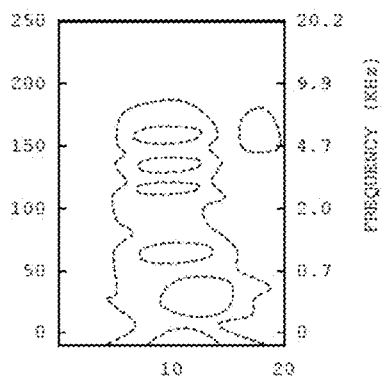
FIG. 4B is a schematic diagram showing a mel-frequency spectrogram according to the embodiment.

Next, in each biogenic sound generation interval, the swallowing estimation part 116a creates a mel-frequency spectrogram as shown in FIG. 4B, from the spectrogram described above. In FIG. 4B, the vertical axis is expressed in the mel-scale. Thus, in the mel-frequency spectrogram shown in FIG. 4B, compared with the frequency spectrogram shown in FIG. 4A, the coordinate axis in low frequency bands is expanded, and the coordinate axis in high frequency bands is compressed. Accordingly, the resolving power for low frequency bands is enhanced.

Figure 4C:
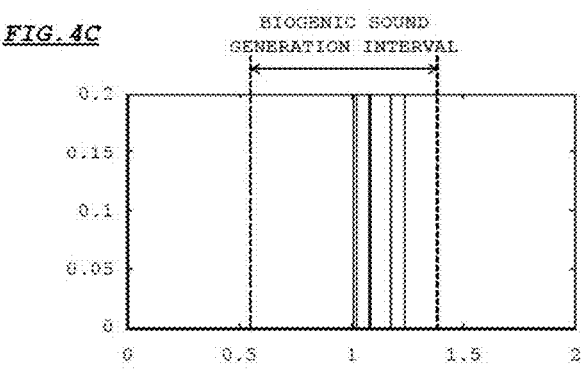
FIG. 4C is a diagram showing pulses obtained through continuous wavelet transform according to the embodiment.
Figure 4D:
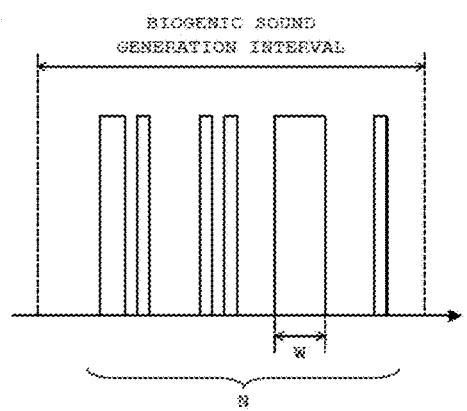
FIG. 4D is an enlarged schematic diagram showing pulses obtained through continuous wavelet transform according to the embodiment.

Next, in each biogenic sound generation interval, the swallowing estimation part 116a performs continuous wavelet transform on the data having been subjected to the short-time Fourier transform described above, to convert the data into pulses, thereby generating the pulses as shown in FIG. 4C. In the example shown in FIG. 4C, the biogenic sound generation interval includes six pulses. In an enlarged schematic representation of these pulses, a plurality of pulses having different widths are included as shown in FIG. 4D.

Next, from among the biogenic sound generation intervals, the swallowing estimation part 116a extracts each biogenic sound generation interval that satisfies all of the following three conditions.

The first condition is that the biogenic sound generation interval includes an amplitude that is greater than or equal to a predetermined threshold. For example, in the example shown in FIG. 3C, an amplitude A1 of the larynx displacement data in the biogenic sound generation interval is large. When the amplitude of the larynx displacement data is large in the biogenic sound generation interval, the first condition is satisfied. During swallowing, the hyoid bone goes up, then, is displaced forward, and then, returns to its original position. The first condition is for determining, on the basis of the larynx displacement data, whether or not such a phenomenon has occurred in the biogenic sound generation interval.

The second condition is that, in the mel-frequency spectrogram of the biogenic sound generation interval, the proportion of the total sum (power) of the spectrum that is higher than or equal to 750 Hz is greater than or equal to a predetermined proportion (for example, 15%). Normally, swallowing sound contains high frequency components. The second condition is for determining, on the basis of the biogenic sound data, whether or not the frequency of sound corresponding to swallowing sound has occurred in the biogenic sound generation interval. For example, with respect to the example shown in FIG. 4B, in the mel-frequency spectrogram of the biogenic sound generation interval, if the proportion of the total sum of the spectrum that is higher than or equal to 750 Hz exceeds 15%, the second condition is satisfied. Here, the threshold is set to 750 Hz, but this threshold can be changed to another frequency as appropriate, by taking statistics of actually measured values of swallowing sound.

The third condition is that the number of pulses shown in FIG. 4C in the biogenic sound generation interval is less than or equal to a predetermined number (for example, 50), and that the maximum width of the pulses generated in the biogenic sound generation interval is less than or equal to a predetermined value (for example, 15 msec). This is because swallowing sound can be distinguished from other sounds from the viewpoint of intermittency and continuity. The higher the intermittency is, the more pulses having short widths appear, and the higher the continuity is, the fewer pulses appear and the longer the pulse width becomes. The third condition is for determining, on the basis of the biogenic sound data, whether or not intermittency and continuity of sound corresponding to swallowing sound have occurred in the biogenic sound generation interval.

For example, with respect to the example shown in FIGS. 4C and 4D, in the biogenic sound generation interval, if the number of pulses N is less than or equal to 50, and the maximum pulse width W is less than or equal to 15 msec, the third condition is satisfied. Here, the threshold for the number of pulses is set to 50 and the threshold for the maximum pulse width is set to 15 msec, but the threshold for the number of pulses and the threshold for the maximum pulse width can be changed to another number and another time width as appropriate, by taking statistics of actually measured values of swallowing sound.

The swallowing estimation part 116a determines whether or not a biogenic sound generation interval satisfying the three conditions above is included in the apneic interval. In general, during swallowing, respiration stops. When a biogenic sound generation interval satisfying the three conditions above is included in the apneic interval, the swallowing estimation part 116a estimates that this biogenic sound generation interval is an interval in which swallowing has occurred.

Among the three conditions above, the first condition (amplitude of larynx displacement) may be excluded. However, if the first condition is included, the accuracy of swallowing estimation can be more enhanced.

<Swallowing Diagnosis Process>

Next, with reference to FIG. 5A to FIG. 7, the process during a swallowing diagnosis is described.

FIG. 5A is a flow chart showing a process of obtaining various types of data.

When the button 112a shown in FIG. 1 is operated and a swallowing diagnosis for a patient is started, the controller 116 causes the pressure sensor 114, the sound sensor 131a, and the displacement sensor 131b to operate, continuously obtains respiratory pressure data, biogenic sound data, and larynx displacement data, and then stores each piece of the obtained data into the storage part 117 as needed (S101 to S103). Until the button 112a is operated again and the swallowing diagnosis ends (S104: YES), the controller 116 continues the processes of steps S101 to S103.

FIG. 5B is a flow chart showing a swallowing diagnosis process. Among the steps included in the flow chart shown in FIG. 5B, steps S201 to S204 are performed by the swallowing estimation part 116a, step S205 is performed by the first swallowing determination part 116b and the second swallowing determination part 116c, and step S206 is performed by the display control part 116d.

When the swallowing diagnosis has been started, the swallowing estimation part 116a sequentially and in real time refers to respiratory pressure data, biogenic sound data, and larynx displacement data which are continuously stored in the storage part 117, and repeats the processes of steps S201 to S203. First, the swallowing estimation part 116a extracts an apneic interval from respiratory pressure data (S201), and extracts a biogenic sound generation interval from biogenic sound data (S202). Then, with respect to the apneic interval and the biogenic sound generation interval that have been extracted, the swallowing estimation part 116a determines whether or not the swallowing condition described with reference to FIG. 3A to FIG. 4D is satisfied (S203). More specifically, the swallowing estimation part 116a determines whether or not the pieces of data in the biogenic sound generation interval satisfy the three conditions above and the biogenic sound generation interval is included in the apneic interval.

When the determination in step S203 is YES, the swallowing estimation part 116a estimates that swallowing has been performed in the biogenic sound generation interval, and sets the biogenic sound generation interval as a swallowing sound generation interval (S204). Upon the estimation that swallowing has occurred, a swallowing determination process by the first swallowing determination part 116b and the second swallowing determination part 116c is performed (S205).

When the swallowing determination process by the first swallowing determination part 116b and the second swallowing determination part 116c has been performed in step S205, the display control part 116d causes the display 111 to display determination results obtained by the first swallowing determination part 116b and the second swallowing determination part 116c (S206). Then, when the swallowing diagnosis process has not ended (S207: NO), the controller 116 returns the process to S201, and performs the same process with respect to each of subsequent data. Accordingly, the display on the display 111 is updated as needed.

<First Swallowing Determination Process>

FIG. 6 is a flow chart showing a first swallowing determination process performed by the first swallowing determination part 116b in step S205 shown in FIG. 5B.

On the basis of the respiratory pressure data stored in the storage part 117, the first swallowing determination part 116b obtains respiratory phases immediately before and immediately after the swallowing sound generation interval (the biogenic sound generation interval in which swallowing has occurred) set in step S204 (S301). Then, the first swallowing determination part 116b determines whether or not the respiratory phase immediately before the swallowing sound generation interval is an inspiratory phase (S302), and further determines whether or not the respiratory phase immediately after this swallowing sound generation interval is an inspiratory phase (S303).

When the first swallowing determination part 116b has determined as YES in either one of S302 and S303, i.e., when the first swallowing determination part 116b has determined that at least one of the respiratory phases before and after the swallowing sound generation interval is an inspiratory phase, the first swallowing determination part 116b determines that there is an aspiration risk in the swallowing sound generation interval (S304). On the other hand, when the first swallowing determination part 116b has determined as NO in both S302 and S303, i.e., when the first swallowing determination part 116b has determined that both of the respiratory phases before and after the swallowing sound generation interval are expiratory phases, the first swallowing determination part 116b determines that there is no aspiration risk in the swallowing sound generation interval (S305).

<Second Swallowing Determination Process>

Figure 7:
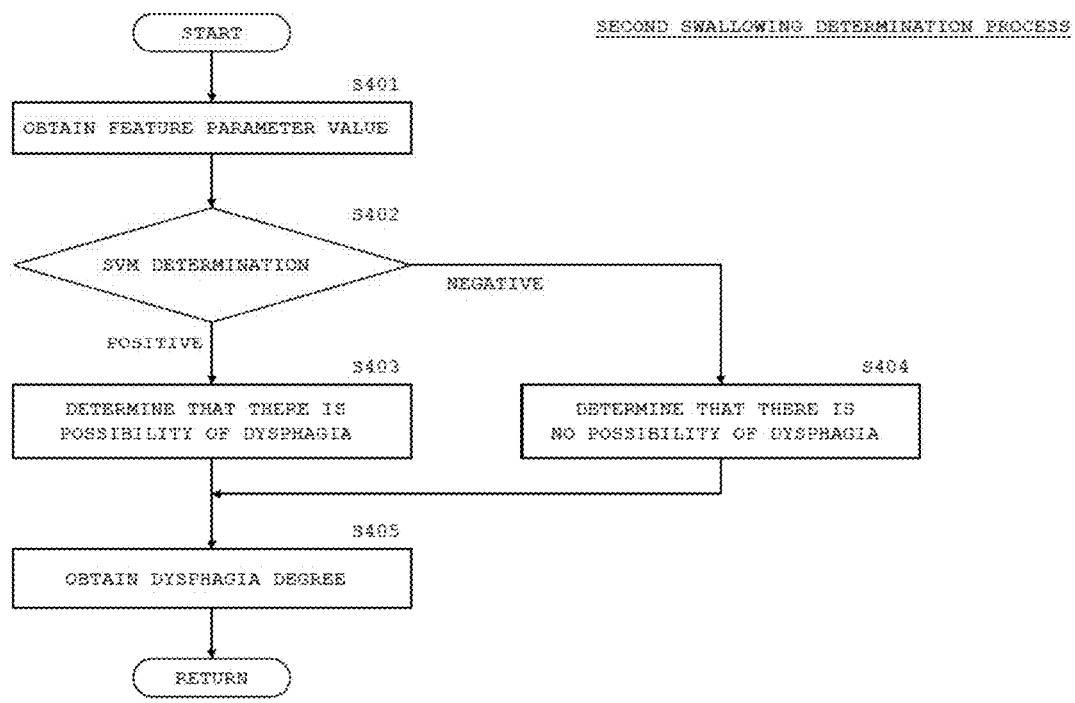
FIG. 7 is a flow chart showing a second swallowing determination process performed in the swallowing diagnosis apparatus according to the embodiment.

FIG. 7 is a flow chart showing a second swallowing determination process performed by the second swallowing determination part 116c in step S205 shown in FIG. 5B.

The second swallowing determination part 116c extracts respiratory pressure data, biogenic sound data, and larynx displacement data in a predetermined interval (hereinafter, referred to as "extraction interval") including the swallowing sound generation interval, and obtains a predetermined feature parameter value (vector) with respect to each extracted data (S401). The feature parameter value obtained here is a parameter value to be handled in a machine learning process by a support vector machine (hereinafter, referred to as "SVM") in the subsequent step S402. For example, the feature parameter value is set as follows.

First, each of the respiratory pressure data, the biogenic sound data, and the larynx displacement data extracted in the extraction interval is subjected to Fourier transform to obtain a frequency spectrum. Next, linear predictive coding (LPC) is applied to the obtained frequency spectrum to obtain a spectrum envelope. Then, the obtained spectrum envelope is sampled at a predetermined frequency interval, and a vector composed of the group of these sample values is obtained as the feature parameter value (feature quantity).

Figure 8:
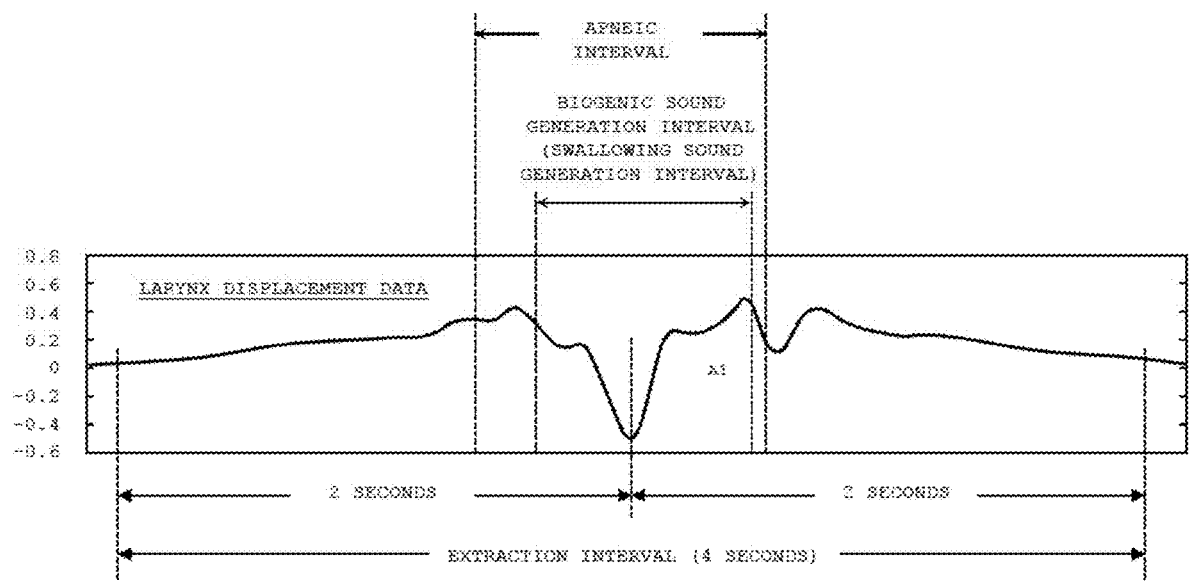
FIG. 8 is a diagram showing a method for setting an extraction interval for various types of data in the second swallowing determination process according to the embodiment.

FIG. 8 is a diagram showing a method for setting the extraction interval for various types of data in the second swallowing determination process.

As shown in FIG. 8, the extraction interval is set so as to include a biogenic sound generation interval (swallowing sound generation interval). Here, the extraction interval is set on the basis of larynx displacement data. That is, an interval having a range of two seconds before and after the position at which the larynx displacement takes the maximum peak in the biogenic sound generation interval is set as the extraction interval.

Here, the extraction interval is set to four seconds, but the time length of the extraction interval is not limited thereto. In general, it is said that the period required in swallowing is about two seconds. Therefore, for obtainment of the feature quantity based on swallowing for each of respiratory pressure data, biogenic sound data, and larynx displacement data, it is sufficient that the extraction interval is set so as to include the biogenic sound generation interval and to have a time length greater than or equal to two seconds. For example, an interval having a range of 1.5 seconds before and after the position at which the larynx displacement takes the maximum peak in the biogenic sound generation interval may be set as the extraction interval. Alternatively, an interval about two seconds from the start timing of the biogenic sound generation interval may be set as the extraction interval, or an interval about three seconds from the timing slightly before the start timing of the biogenic sound generation interval may be set as the extraction interval.

With reference back to FIG. 7, when the second swallowing determination part 116c has obtained the feature parameter value from each of the respiratory pressure data, the biogenic sound data, and the larynx displacement data in step S401, the second swallowing determination part 116c performs the machine learning process by the SVM on the basis of the obtained feature parameter value (vector), and determines which of a dysphagia positive region and a dysphagia negative region the feature parameter value belongs to (S402).

The storage part 117 shown in FIG. 2 has stored therein a teaching data group (a dysphagia-positive sample data group and a dysphagia-negative sample data group) to be used in the machine learning process by the SVM. On the basis of the teaching data group stored in the storage part 117, the second swallowing determination part 116c sets a boundary which separates dysphagia positive from dysphagia negative in the SVM. Alternatively, instead of the teaching data group, data that specifies a boundary which separates dysphagia positive from dysphagia negative in the SVM may be stored in the storage part 117.

When the feature parameter value belongs to the positive region (S402: positive), the second swallowing determination part 116c determines that there is a possibility of dysphagia (S403). When the feature parameter value belongs to the negative region (S402: negative), the second swallowing determination part 116c determines that there is no possibility of dysphagia (S404). Further, the second swallowing determination part 116c obtains a dysphagia degree (degree of positive/negative) with respect to the feature parameter value (S405).

Here, the dysphagia degree is obtained according to how much the feature parameter value is separated from the boundary between the positive region and the negative region in the SVM. That is, in a case where the feature parameter value is included in the negative region, if the distance between the position of the feature parameter value and the boundary is larger, the negative degree is higher. In a case where the feature parameter value is included in the positive region, if the distance between the position of the feature parameter value and the boundary is larger, the positive degree is higher.

The inventors of the present application have conducted various studies on the feature parameter value obtained in the second swallowing determination part 116c and have made thorough investigation on what feature parameter value is preferable to be used in the dysphagia determination. In the following, examination results of the studies are described.

<Examination 1>

In Examination 1, the relationship between the dysphagia determination accuracy and the feature parameter was studied. Here, as the feature parameter, LPC spectrum and LPC coefficient were studied, and as a comparison, MFCC (mel-frequency cepstrum coefficient) was studied.

First, with reference to FIGS. 9A and 9B, a method for obtaining the feature parameter value based on the LPC spectrum and a method for obtaining the feature parameter value based on the LPC coefficient are described.

For convenience, FIGS. 9A and 9B each show a frequency spectrum obtained by subjecting waveform data based on a predetermined sound to Fourier transform, and a spectrum envelope obtained by applying linear predictive coding (LPC) to this frequency spectrum. In FIGS. 9A and 9B, spectrum envelopes obtained when the maximum orders of the arithmetic expression for the linear predictive coding are respectively set to 8 and 16 are shown.

In the obtainment of the parameter value based on the LPC spectrum, first, Fourier transform is applied to the target waveform data, and the frequency spectrum corresponding to the waveform data is obtained. Next, linear predictive coding (LPC) is applied to the obtained frequency spectrum to obtain a spectrum envelope, and then, the obtained spectrum envelope is sampled at a predetermined frequency interval, to obtain sample values. For example, the spectrum envelopes shown in FIGS. 9A and 9B are sampled at a cycle of 10 Hz in the horizontal axis, and the power value of the spectrum envelope in each sampling is obtained. The group of thus-obtained power values is obtained as the parameter value (vector) based on the LPC spectrum.

In FIGS. 9A and 9B, since the orders of the arithmetic expression in the linear predictive coding are different, the waveforms of the obtained spectrum envelopes are different from each other. Therefore, in FIGS. 9A and 9B, the parameter values (vectors) obtained on the basis of the LPC spectra are different from each other. The higher the order of the arithmetic expression is, the finer spectrum envelope is obtained along the frequency spectrum, and thus, a feature parameter value that more matches the frequency spectrum is likely to be obtained. However, if the order of the arithmetic expression is excessively high, the influence of noise is likely to appear on the spectrum envelope, and thus, the feature parameter value is also likely to be affected by the noise. Therefore, in the case of the feature parameter based on the LPC spectrum, what order is to be set for the arithmetic expression is important.

In the linear predictive coding described above, the coefficient at each order of the arithmetic expression is adjusted to obtain a spectrum envelope. Therefore, when the frequency spectrum is different, the coefficient at each order of the arithmetic expression is also different, and when the order of the arithmetic expression is different, the coefficient at each order is also different. As for the feature parameter based on the LPC coefficient, the group of coefficients at each order in the arithmetic expression when linear predictive coding is applied to the frequency spectrum is obtained as the feature parameter value (vector).

In Examination 1, with respect to the frequency spectra obtained by subjecting, to Fourier transform, the respiratory pressure data, the biogenic sound data, and the larynx displacement data extracted in the extraction interval, the feature parameter value (vector) was obtained on the basis of the LPC spectrum, the LPC coefficient, and the MFCC. Here, the extraction interval was set to two seconds from the start of the biogenic sound generation interval, not the extraction interval (four seconds) shown in FIG. 8.

In the case of the LPC spectrum and the LPC coefficient, the parameter value when the maximum order of the arithmetic expression was set to 8, 16, 32 was obtained, and with respect to the parameter value at each order, dysphagia positive/negative was evaluated through the machine learning process by the SVM. RBF (Radial Basis Function) was used as the kernel for the SVM.

Examination by cross-validation (10-fold cross validation) was performed on 178 pieces of sample data in total composed of: 114 pieces of sample data (respiratory pressure data, biogenic sound data, and larynx displacement data) obtained from healthy subjects; and 64 pieces of sample data (respiratory pressure data, biogenic sound data, and larynx displacement data) obtained from patients.

FIGS. 10A to 10C are each a diagram showing examination results obtained when the LPC spectrum was used as the feature parameter in Examination 1. FIGS. 11A to 11C are each a diagram showing examination results obtained when the coefficient at an LPC order was used as the feature parameter in Examination 1. FIGS. 12A to 12C are each a diagram showing examination results obtained when MFCC was used as the feature parameter in Examination 1.

FIGS. 13A to 13C are each a diagram summarizing the examination results of Examination 1 according to the type of data (larynx displacement, respiratory pressure, swallowing sound). In FIGS. 13A to 13C, the healthy subject determination accuracy is the determination accuracy at which samples of healthy subjects were determined as dysphagia negative, and the patient determination accuracy is the determination accuracy at which samples of patients were determined as dysphagia positive.

FIG. 10A to FIG. 11C, and FIGS. 13A to 13C show the determination results having the highest determination accuracies among the determination results obtained by use of the LPC spectrum and the LPC coefficient when the order of the arithmetic expression was 8, 16, 32.

With reference to FIG. 10A to FIG. 13C, when the LPC spectrum and the LPC coefficient were used as the feature parameter, in any case where the larynx displacement data, the respiratory pressure data, or the biogenic sound data was used, the healthy subject determination accuracy and the patient determination accuracy were high, compared with those when the MFCC was used. In particular, when the LPC spectrum was used as the feature parameter, there was a tendency that the healthy subject determination accuracy and the patient determination accuracy were high, compared with those when the other feature parameters were used. Therefore, it can be said that, as the feature parameter for dysphagia determination, the LPC spectrum and the LPC coefficient are effective, and in particular, the LPC spectrum is effective.

<Examination 2>

In Examination 2, it was examined how the dysphagia determination accuracy differs between the cases where the value of the feature parameter (vector) was obtained in a non-time series manner and in a time series manner. The method for obtaining the feature parameter described with reference to FIGS. 9A and 9B is a non-time-series obtaining method.

In the time-series obtaining method, the frequency spectrum shown in FIG. 9A, 9B is divided into a plurality of frequency bands, and linear predictive coding is applied for each frequency band. For example, in the case of FIG. 9A, 9B, the frequency spectrum extending in the frequency region of about 0 to 23000 Hz is divided into about 23 frequency bands for each 100 Hz in the horizontal axis, and linear predictive coding is individually applied for each frequency band and a spectrum envelope is obtained. Thus-obtained spectrum envelope is sampled at a predetermined frequency interval, similar to the above, and a feature parameter value (vector) based on the LPC spectrum is obtained.

In the time-series obtaining method, linear predictive coding is applied for each divided frequency band, whereby a spectrum envelope is obtained. Therefore, the obtained spectrum envelope is different from that according to the non-time-series obtaining method. Therefore, the feature quantity (vector) of the LPC spectrum obtained by the time-series obtaining method is different from the feature quantity (vector) of the LPC spectrum obtained by the non-time-series obtaining method.

In Examination 2, with respect to the frequency spectra obtained by subjecting, to Fourier transform, the respiratory pressure data, the biogenic sound data, and the larynx displacement data extracted in the extraction interval, the feature parameter values (vector) were obtained on the basis of the LPC spectra according to the time-series method and the non-time-series method. Also here, the extraction interval was set to two seconds from the start of the biogenic sound generation interval, not the extraction interval (four seconds) shown in FIG. 8.

The parameter value when the maximum order of the arithmetic expression for the LPC spectrum was set to 8, 16, 32 was obtained according to the non-time-series method and the time-series method, and with respect to the parameter value of each order, dysphagia positive/negative was evaluated through the machine learning process by the SVM. RBF (Radial Basis Function) was used as the kernel for the SVM. Examination by cross-validation (10-fold cross validation) was performed on 768 pieces of sample data in total composed of: 556 pieces of sample data (respiratory pressure data, biogenic sound data, and larynx displacement data) obtained from healthy subjects; and 212 pieces of sample data (respiratory pressure data, biogenic sound data, and larynx displacement data) obtained from patients.

FIG. 14 is a diagram showing, by numerical values, the examination results obtained when the feature parameter value was obtained on the basis of the LPC spectrum according to the non-time-series method. FIG. 15 is a diagram showing, by numerical values, the examination results obtained when the feature parameter value was obtained on the basis of the LPC spectrum according to the time-series method. In FIGS. 14 and 15, the LPC order indicates the maximum order of the arithmetic expression of linear predictive coding. In FIGS. 14 and 15, the healthy subject determination accuracy is the determination accuracy at which samples of healthy subject were determined as dysphagia negative, and the patient determination accuracy is the determination accuracy at which samples of patients were determined as dysphagia positive.

With reference to FIG. 14 and FIG. 15, in the cases where the feature parameter value was obtained on the basis of the LPC spectrum according to the time-series method, the patient determination accuracy was significantly increased, compared with that in the cases where the feature parameter value was obtained on the basis of the LPC spectrum according to the non-time-series method. In the case of the time-series method, the determination accuracy where the LPC order was 32 was increased, compared with that of the non-time-series method. From this, it can be said that, if the LPC spectrum is used as the feature parameter for dysphagia determination, it is effective to obtain the feature parameter value by the time-series obtaining method.

<Examination 2-2>

Next, according to a method similar to that in Examination 2, dysphagia determination was performed on 637 pieces of sample data (biogenic sound data) obtained from healthy subjects and 5 pieces of sample data (biogenic sound data) obtained from patients, by the SVM which had learned using the parameter having the highest dysphagia determination accuracy in Examination 2. In Examination 2-2, for each sample, the age of the sample provider was set.

Figure 16:
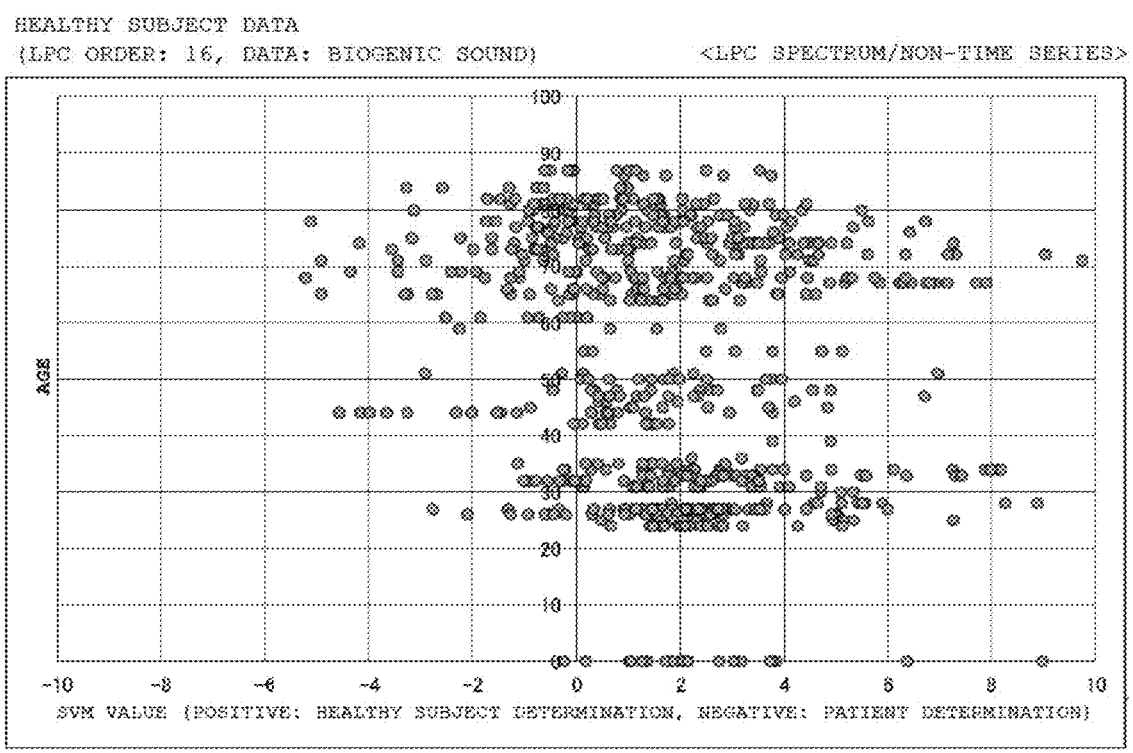
FIG. 16 is a graph showing the examination result obtained with respect to healthy subject data when the feature parameter value was obtained on the basis of the LPC spectrum according to the non-time-series method in Examination 2 according to the embodiment.

FIG. 16 is a graph showing the examination result obtained with respect to healthy subject data when the feature parameter value was obtained on the basis of the LPC spectrum according to the non-time-series method in Examination 2-2. FIG. is a graph showing the examination result obtained with respect to patient data when the feature parameter value was obtained on the basis of the LPC spectrum according to the non-time-series method in Examination 2-2.

Figure 18:
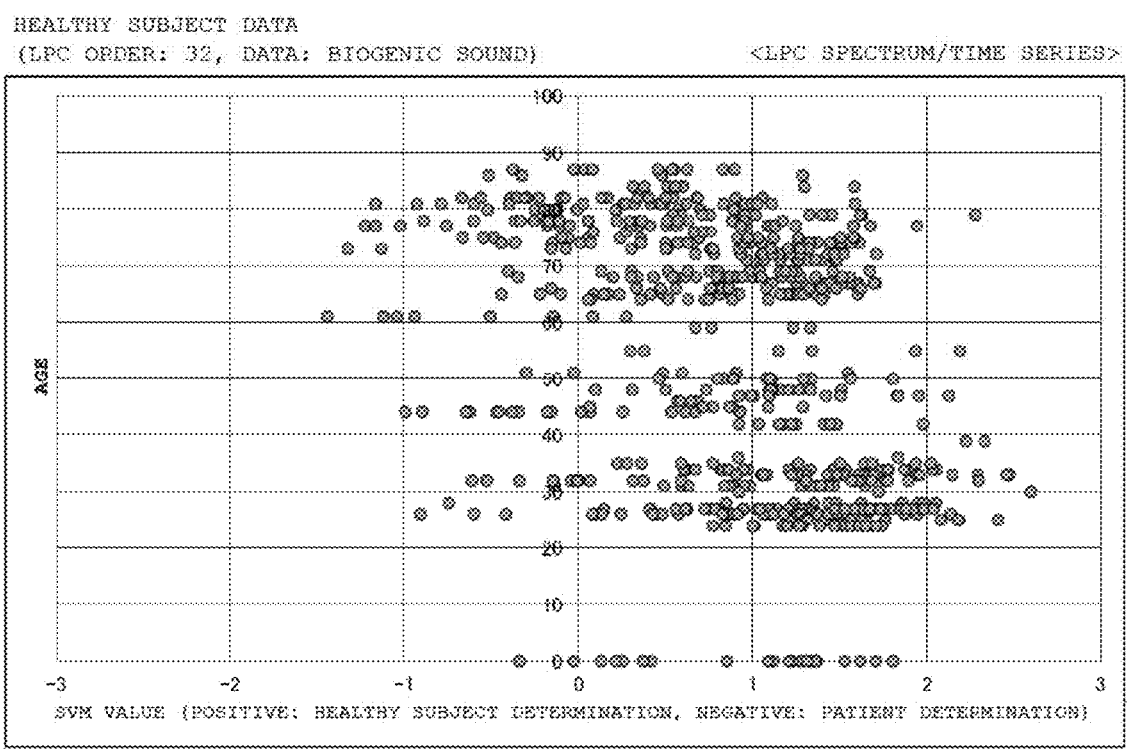
FIG. 18 is a graph showing the examination result obtained with respect to healthy subject data when the feature parameter value was obtained on the basis of the LPC spectrum according to the time-series method in Examination 2 according to the embodiment.
Figure 19:
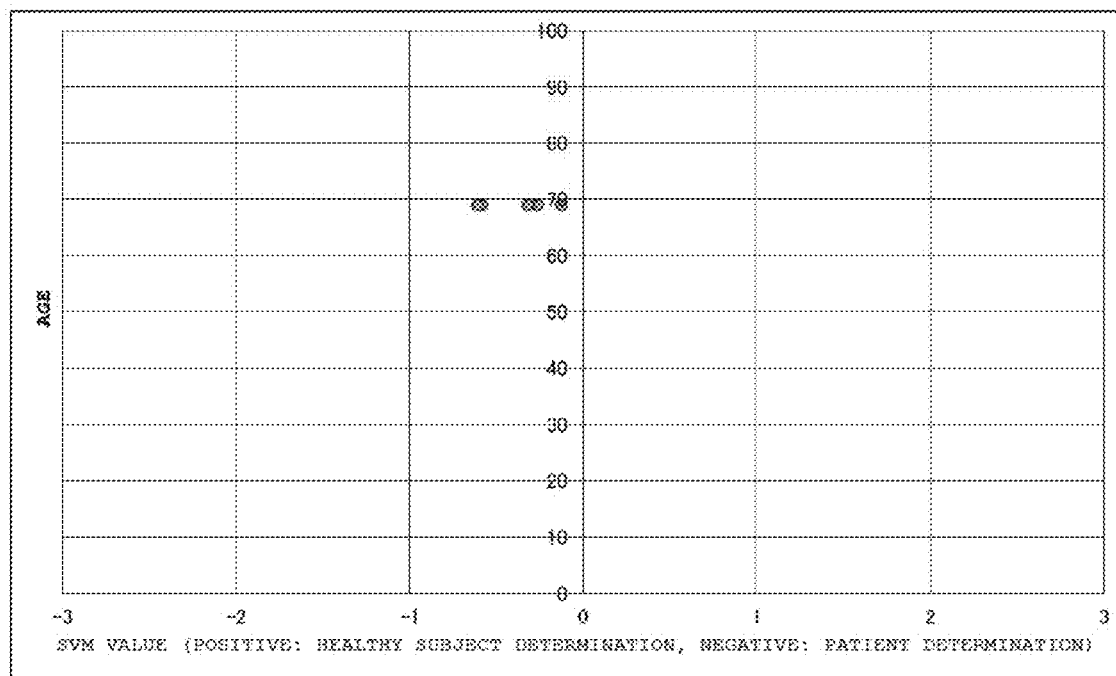
FIG. 19 is a graph showing the examination result obtained with respect to patient data when the feature parameter value was obtained on the basis of the LPC spectrum according to the time-series method in Examination 2 according to the embodiment.

FIG. 18 is a graph showing the examination result obtained with respect to healthy subject data when the feature parameter value was obtained on the basis of the LPC spectrum according to the time-series method in Examination 2-2. FIG. 19 is a graph showing the examination result obtained with respect to patient data when the feature parameter value was obtained on the basis of the LPC spectrum according to the time-series method in Examination 2-2.

Figure 17:
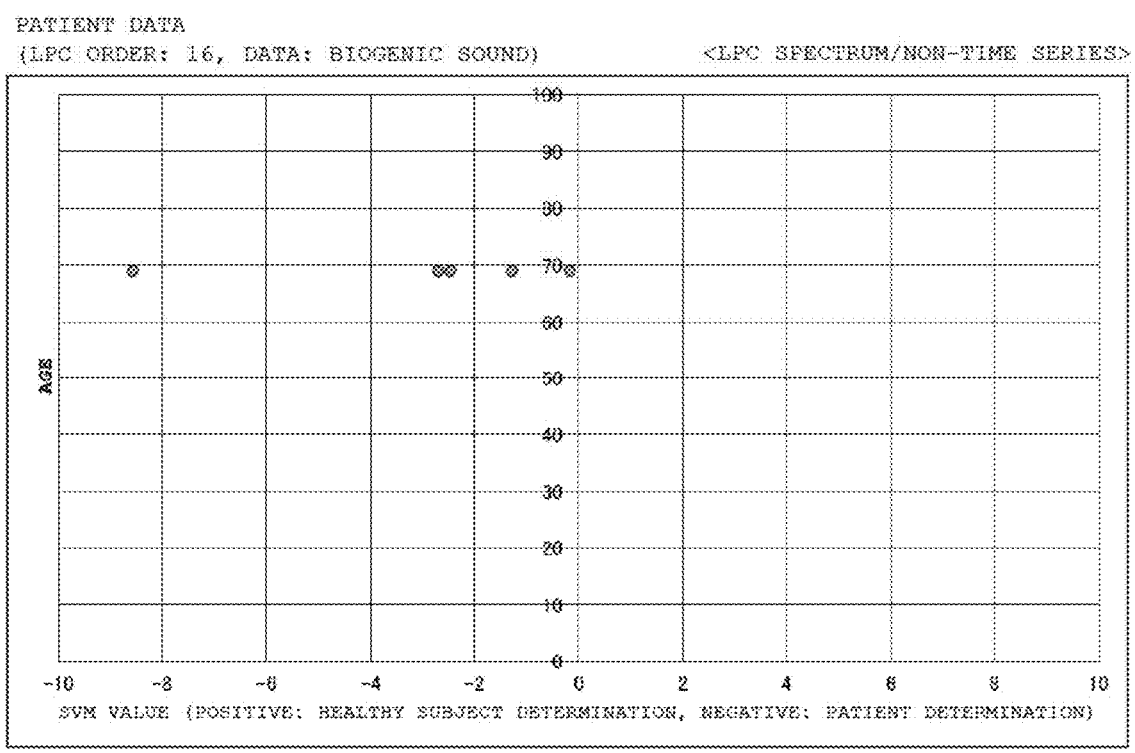
FIG. 17 is a graph showing the examination result obtained with respect to patient data when the feature parameter value was obtained on the basis of the LPC spectrum according to the non-time-series method in Examination 2 according to the embodiment.

In FIG. 16 to FIG. 18, the horizontal axis represents the value of the SVM, and the vertical axis represents the age. In FIG. 16 to FIG. 18, for each sample, the value of the SVM obtained from the sample is plotted. When the value of the SVM is a positive value, the sample is determined as that of a healthy subject (dysphagia: negative). When the value of the SVM is a negative value, the sample is determined as that of a patient (dysphagia: positive).

When FIGS. 16 and 17 (non-time series) and FIGS. 18 and 19 (time series) are compared, it can be confirmed that the determination accuracy for healthy subjects is slightly higher in the time-series obtaining method for the feature parameter, than that in the non-time-series obtaining method. The determination accuracy for patients is 100% in both of the time-series case and the non-time-series case.

It is also seen that the dispersion of the SVM values in the horizontal axis direction is more suppressed in the time-series obtaining method for the feature parameter, than in the non-time-series method. Further, in the determination with respect to the healthy subject data, the plot group of the SVM values is more separated in the positive-value direction (more dysphagia-negative direction) from the boundary line (the line at SVM value=0) between dysphagia-negative and dysphagia-positive in the time-series obtaining method for the feature parameter, than in the non-time-series method. From this, it can be said that the dysphagia determination accuracy is higher and the degree of dysphagia can be obtained at higher accuracy in the time-series obtaining method for the feature parameter, than in the non-time-series method.

FIG. 20A is a diagram summarizing, in a table, the examination results of Examination 2. FIG. 20A shows the determination result having the highest accuracy (LPC order=16, data type=biogenic sound data) in the determination result according to the non-time-series method in FIG. 14, and the determination result having the highest accuracy (LPC order=32, data type=biogenic sound data) in the determination result according to the time-series method in FIG. 15.

With reference to the summary in FIG. 20A and the determination results in FIG. 14 to FIG. 19, it is seen that the dysphagia determination accuracy is higher when the LPC spectrum is obtained by the time-series obtaining method than when the LPC spectrum is obtained by the non-time-series obtaining method. Therefore, for obtainment of the feature parameter value, it can be said that it is preferable to use the time-series obtaining method.

With reference to FIG. 14 and FIG. 15, as for the type of the data that contributes to the dysphagia determination accuracy, there is a tendency that the swallowing sound data contributes most and the respiratory pressure data contributes next. Therefore, for obtainment of the feature parameter value, it can be said that it is preferable to use the swallowing sound data most preferentially, and to use the respiratory pressure data next preferentially.

In Examination 2, with respect to obtainment of the feature parameter on the basis of the LPC spectrum, the difference in the determination accuracy according to the non-time-series obtaining method and the time-series obtaining method was examined. However, also with respect to obtainment of the feature parameter on the basis of the LPC coefficient, it can be assumed that there is a tendency similar to that described above. Also in the case of obtaining the feature parameter on the basis of the LPC coefficient, it can be assumed that the dysphagia determination accuracy is higher in the time-series obtaining method, than in the non-time-series obtaining method.

<Examination 3>

In Examination 3, it was examined how the dysphagia determination accuracy changed in a case where: the feature parameter values (vectors) respectively obtained from respiratory pressure data, biogenic sound data, and larynx displacement data were combined into one feature parameter value (vector); and the machine learning process by the SVM was performed on the combined feature parameter value.

Obtainment of the feature parameter value from each data was performed on the basis of the LPC spectrum according to the time-series method. Also here, the extraction interval was set to two seconds from the start of the biogenic sound generation interval, not the extraction interval (four seconds) shown in FIG. 8.

With respect to respiratory pressure data, biogenic sound data, and larynx displacement data, the parameter value when the maximum order of the arithmetic expression for the LPC spectrum was set to 8, 16, 32 was obtained according to the time-series method. Then, the obtained parameter values of the respective data were combined, at each order, to obtain one feature parameter value. Then, with respect to the feature parameter value at each order, dysphagia positive/negative was evaluated through the machine learning process by the SVM. RBF (Radial Basis Function) was used as the kernel for the SVM. 768 pieces of sample data in total composed of: 556 pieces of sample data (respiratory pressure data, biogenic sound data, and larynx displacement data) obtained from healthy subjects; and 212 pieces of sample data (respiratory pressure data, biogenic sound data, and larynx displacement data) obtained from patients, were used as sample data. The examination by cross-validation (10-fold cross validation) was performed.

FIG. 20B is a diagram showing the examination results of Examination 3.

When the examination results shown in FIG. 20B and the examination results shown in FIG. 20A are compared with each other, the dysphagia determination accuracy was higher in the case where the machine learning process by the SVM was performed using the combination of the feature parameter values obtained from the three data, than in the case where the machine learning process by the SVM was performed using the feature parameter value obtained from biogenic sound data only. In particular, when the LPC order was 32, the dysphagia determination accuracy was significantly higher in the case of the combination of the three data, than in the case where biogenic sound data only was used. From this, it can be said that, in dysphagia determination, it is preferable to perform the machine learning process by the SVM while using a combination of the feature parameter values obtained from respiratory pressure data, biogenic sound data, and larynx displacement data.

<Examination 3-2>

With respect to 637 pieces of sample data obtained from healthy subjects and 5 pieces of sample data obtained from patients, dysphagia determination was performed according to a method similar to that of Examination 3, by the SVM which had learned using the parameter having the highest dysphagia determination accuracy in Examination 3. In Examination 3-2, for each sample, the age of the sample provider was set.

Figure 21:
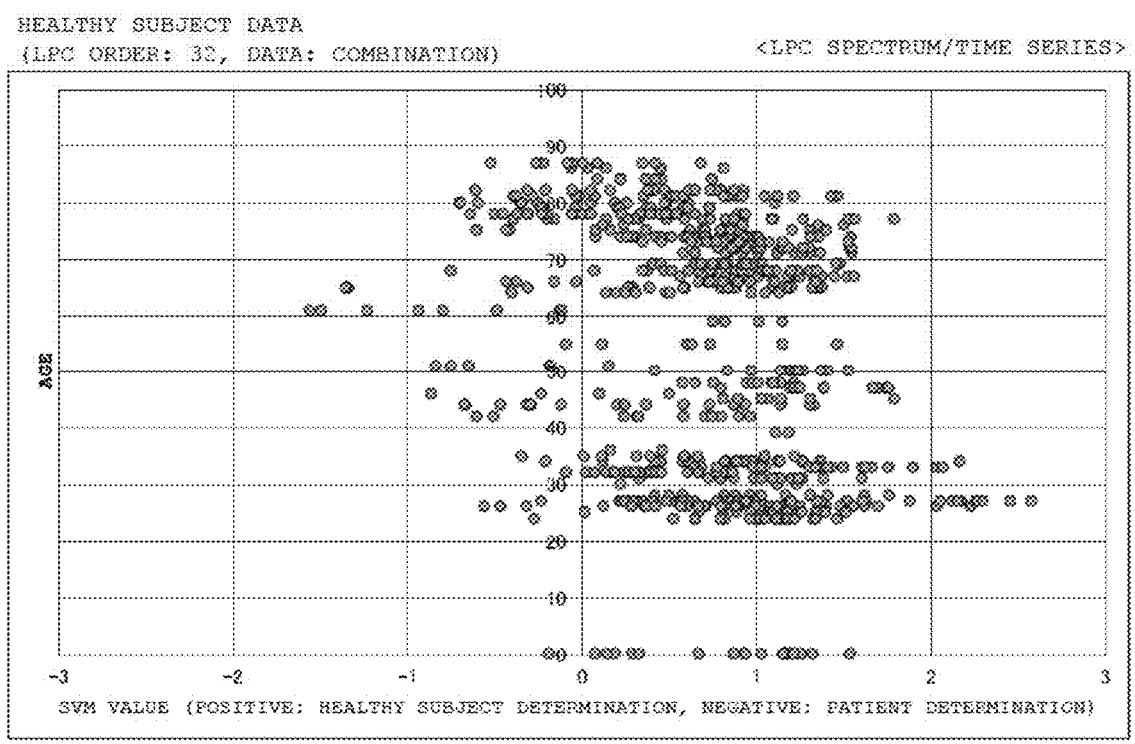
FIG. 21 is a graph showing the examination result obtained with respect to healthy subject data when extraction of the feature quantity was performed by use of the LPC spectrum according to the time-series method in Examination 3 of the embodiment.

FIG. 21 is a graph showing the determination result obtained when dysphagia determination was performed with respect to the healthy subject data in Examination 3-2. FIG.

Figure 22:
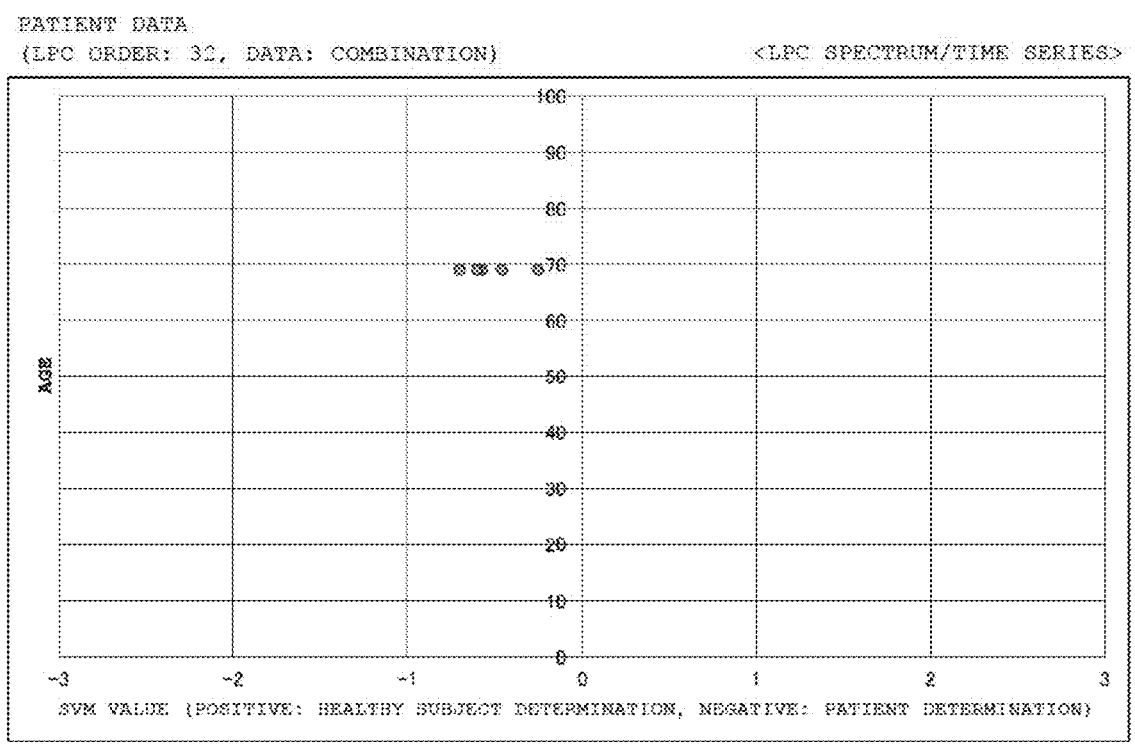
FIG. 22 is a graph showing the examination result obtained with respect to patient data when extraction of the feature quantity was performed by use of the LPC spectrum according to the time-series method in Examination 3 according to the embodiment.

22 is a graph showing the examination result obtained when dysphagia determination was performed with respect to the patient data in Examination 3-2. In FIGS. 21 and 22, similar to FIG. 16 to FIG. 18, the horizontal axis represents the value of the SVM, and the vertical axis represents the age.

When FIG. 21 and FIG. 18 are compared with each other, it is seen that the dispersion of the SVM values in the horizontal axis direction is more suppressed and the variation in the evaluation according to age group is more suppressed in the case where the three types of feature parameter values are combined, than in the case where one type of feature parameter value only is used. From this, it can be said that the variation in the dysphagia determination according to age group can be more suppressed and the degree of dysphagia can be obtained at higher accuracy in the case where the three types of feature parameter values are combined, than in the case where one type of feature parameter value only is used.

On the basis of the examination above, in step S401 in FIG. 7, a feature parameter which is a combination of the three types of feature parameters is obtained, and in step S402, SVM determination using the combined feature parameter is performed. That is, in step S401, the second swallowing determination part 116c obtains, as a feature parameter value, the feature parameter value shown in Examination 3, i.e., the combination of parameter values which are based on the LPC spectra according to the time-series method and which are respectively obtained from respiratory pressure data, biogenic sound data, and larynx displacement data. Then, in step S402, the second swallowing determination part 116c determines the presence or absence of dysphagia through the machine learning process by the SVM on the basis of the obtained feature parameter value. Then, in accordance with the determination result, the second swallowing determination part 116c determines the presence or absence of possibility of dysphagia in step S403 or step S404.

In step S405, the second swallowing determination part 116c obtains the dysphagia degree on the basis of the distance of the feature parameter value with respect to the boundary between the dysphagia positive region and the dysphagia negative region in the SVM. This distance corresponds to, for example, the distance between the plots in FIG. 21, 22 and the axis where the value of the SVM is zero.

<Diagnosis Result Screen>

FIG. 23A is a diagram showing a configuration of a display screen for a diagnosis result to be displayed in step S206 in FIG. 5B. FIGS. 23B to 23E are each a diagram showing a display form of a first determination result.

As shown in FIG. 23A, a display screen 200 for a diagnosis result includes a swallowing estimation mark 201, a cough detection mark 202, a first determination result region 203, and a second determination result region 204.

As for the swallowing estimation mark 201, the periphery thereof is lit in a predetermined color (for example, blue) when occurrence of swallowing has been estimated in step S204 in FIG. 5B. As for the cough detection mark 202, a center portion thereof is lit in a predetermined color (for example, orange) if there is choking due to aspiration when occurrence of swallowing has been estimated in step S204 in FIG. 5B. Here, choking is detected by the controller 116 on the basis of the respiratory pressure data.

In the first determination result region 203, a determination result obtained by the first swallowing determination part 116b is displayed. Specifically, the respiratory phases before and after the swallowing sound generation interval obtained in step S301 in FIG. 6 are displayed together with arrows showing shifts with respect to swallowing. The background color of the first determination result region 203 is set in accordance with the aspiration risk determination result in step S304, S305 in FIG. 6. Specifically, when there is no aspiration risk, the background color of the first determination result region 203 is set to a first color (for example, green) as shown in FIG. 23B. When there is an aspiration risk, the background color of the first determination result region 203 is set to a second color (for example, red) as shown in FIGS. 23C to 23E.

On the basis of the description and the background color in the first determination result region 203, the user such as a doctor can appropriately understand the possibility of aspiration risk and the shift of the respiratory phase.

In the second determination result region 204, the determination result obtained by the second swallowing determination part 116c is displayed. In the second determination result region 204, ten cursors arranged in the horizontal direction, and descriptions and arrows indicating the magnitude of the dysphagia degree are shown. The cursors are set such that the shading degrees thereof are increased leftward. When it has been determined that there is no possibility of dysphagia in the flow chart shown in FIG. 7, five cursors at the right side in the second determination result region 204 are lit in accordance with the dysphagia degree. When it has been determined that there is a possibility of dysphagia in the flow chart shown in FIG. 7, five cursors at the left side are lit in accordance with the dysphagia degree.

For example, if the polarity of the dysphagia degree is set such that the dysphagia positive is expressed by a positive value and the dysphagia negative is expressed by a negative value, when the dysphagia degree is −3, the three cursors at the right side from the center of the second determination result region 204 are lit, and when the dysphagia degree is +4, the four cursors at the left side from the center of the second determination result region 204 are lit. As described above, the level of the dysphagia degree is determined on the basis of the distance between the feature parameter and the boundary which separates the dysphagia positive from the dysphagia negative in the SVM.

On the basis of the state of the cursors and the description in the second determination result region 204, the user such as a doctor can appropriately understand the possibility of dysphagia.

<Teaching Data Update System>

In the embodiment above, the possibility of dysphagia is determined through the machine learning process by the SVM. In this case, if teaching data of good quality is used in a greater amount, the boundary between positive and negative can be finely set, and the dysphagia determination accuracy can be enhanced.

Figure 24:
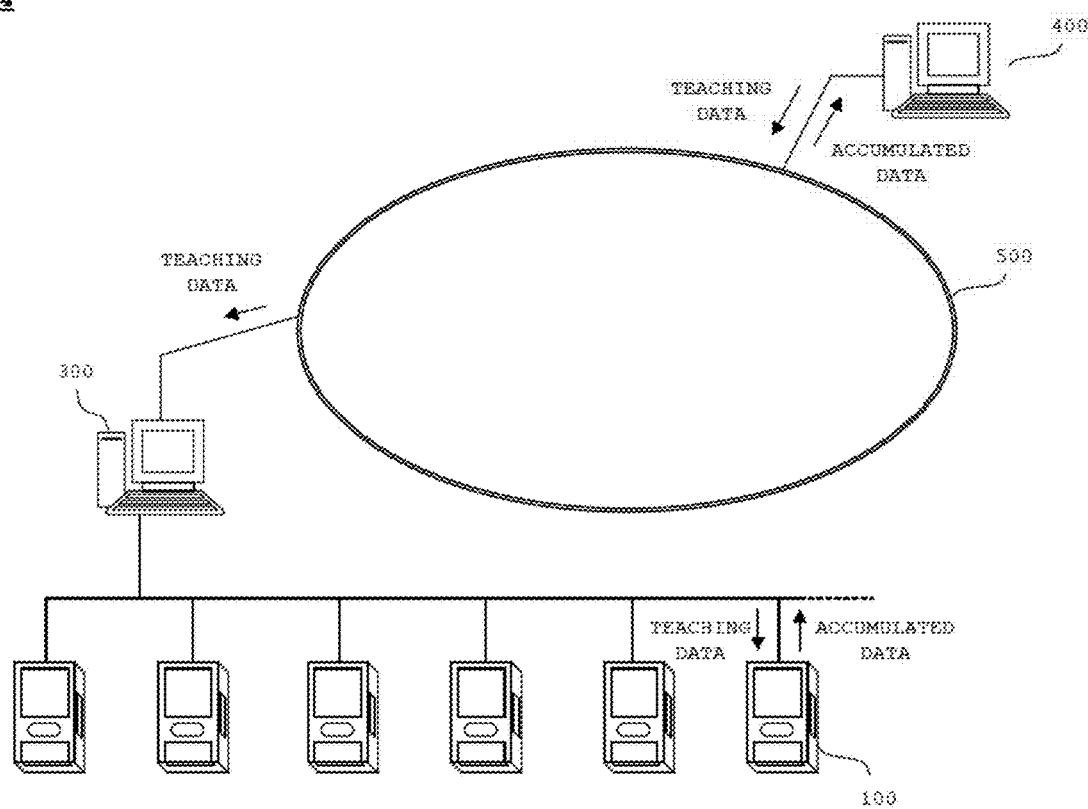
FIG. 24 is a schematic diagram showing a configuration of a system for updating teaching data to be used by a second swallowing determination part in the swallowing diagnosis apparatus according to the embodiment.

FIG. 24 is a schematic diagram showing a configuration of a system for updating the teaching data to be used by the second swallowing determination part 116c in the swallowing diagnosis apparatus 100.

In this system, respiratory pressure data, biogenic sound data, and larynx displacement data (those extracted in the extraction interval including the swallowing sound generation interval) obtained in each swallowing diagnosis apparatus 100 during diagnosis for patients are intensively stored in a host computer 300 installed in a medical institution such as a hospital. Each user such as a doctor inputs a dysphagia diagnosis result for a patient concerned, in association with these types of data. The host computer 300 transmits the intensively-stored data together with the diagnosis results, to a server 400 in a management facility via an external network 500.

In the management facility, an operator classifies the data received by the server 400 into teaching data for dysphagia positive, teaching data for dysphagia negative, and ineffective data, on the basis of the diagnosis results. Then, the operator accumulates the classified positive and negative data into a database in the server 400. The server 400 periodically transmits the teaching data accumulated in the database to the host computer 300 at the medical institution side. The host computer 300 provides the received teaching data to each swallowing diagnosis apparatus 100. Accordingly, the teaching data stored in each swallowing diagnosis apparatus 100 is updated. As a result, the dysphagia determination accuracy by the second swallowing determination part 116c is enhanced.

<Effects of the Embodiment>

According to the swallowing diagnosis apparatus 100 of the present embodiment, the risk of aspiration that could occur as a result of characteristics (habit, etc.) of an individual being modified due to the age or diseases is determined by the first swallowing determination part 116b, and the possibility of dysphagia is determined by the second swallowing determination part 116c. Then, these determination results are displayed on the display 111 to be presented to the user such as a doctor. Accordingly, by referring to these determination results, the user such as a doctor can determine the aspiration risk in the patient multilaterally and comprehensively, and can diagnose the aspiration risk in the patient more appropriately.

In the determination by the first swallowing determination part 116b, a determination result indicating aspiration is caused as a result of the characteristic (habit, etc.) of an individual being modified due to the age or diseases. However, this determination result is a risk factor for Parkinson's disease, and a recent study of the inventors has clarified that the determination result is an excellent related factor for aggravation of COPD (chronic obstructive pulmonary disease). Therefore, even in a case where the second swallowing determination part 116c has not determined that there is a possibility of dysphagia, if the first swallowing determination part 116b has determined that there is an aspiration risk, it is necessary to take measures in accordance with the state of the patient.

In contrast, since the determination in the first swallowing determination part 116b is based on the characteristics of an individual, even if the first swallowing determination part 116b has determined that there is no aspiration risk, there is naturally a case where the second swallowing determination part 116c determines that there is a possibility of dysphagia. Also in such a case, it is necessary to take measures in accordance with the state of the patient.

As described above, the determination result obtained in the first swallowing determination part 116b and the determination result obtained in the second swallowing determination part 116c are both independently meaningful in determination of the swallowing state, and function complementarily with each other. Therefore, if the user such as doctor sequentially refers to these determination results on the display screen 200 shown in FIG. 23A, the user can determine the aspiration risk in the patient multilaterally and comprehensively, and can more appropriately take measures for the patient.

According to the swallowing diagnosis apparatus 100 of the present embodiment, the determination in the first swallowing determination part 116b and the determination in the second swallowing determination part 116c are performed, using respiratory pressure data, biogenic sound data, larynx displacement data obtained for swallowing estimation. Thus, there is no need to separately obtain data from the patient for these determinations. Therefore, the configuration of the swallowing diagnosis apparatus 100 can be simplified, and the processing load in these determinations can be reduced.

According to the swallowing diagnosis apparatus 100 of the present embodiment, the LPC spectrum based on biogenic sound data is included as a feature parameter. Thus, as shown in Examination 2, the determination accuracy regarding the possibility of dysphagia in the second swallowing determination part 116c can be enhanced.

According to the swallowing diagnosis apparatus 100 of the present embodiment, the LPC spectrum based on respiratory pressure data as well as biogenic sound data is included as a feature parameter. Thus, as shown in Examination 2, the determination accuracy regarding the possibility of dysphagia in the second swallowing determination part 116c can be further enhanced.

According to the swallowing diagnosis apparatus 100 of the present embodiment, a combination of LPC spectra based on biogenic sound data, respiratory pressure data, and larynx displacement data is used as a feature parameter. Thus, as shown in Examination 3, the determination accuracy regarding the possibility of dysphagia in the second swallowing determination part 116c can be further enhanced.

According to the swallowing diagnosis apparatus 100 of the present embodiment, the LPC spectrum is used as a feature parameter. Thus, as shown in Examination 1, the determination accuracy regarding the possibility of dysphagia in the second swallowing determination part 116c can be enhanced.

According to the swallowing diagnosis apparatus 100 of the present embodiment, the LPC spectrum according to the time-series method is used as a feature parameter. Thus, as shown in Examination 2, the determination accuracy regarding the possibility of dysphagia in the second swallowing determination part 116c can be further enhanced.

As shown in Examination 1, also in a case where the LPC coefficient is used as a feature parameter instead of the LPC spectrum, the determination accuracy regarding the possibility of dysphagia in the second swallowing determination part 116c can be enhanced.

<Modification>

Figure 25:
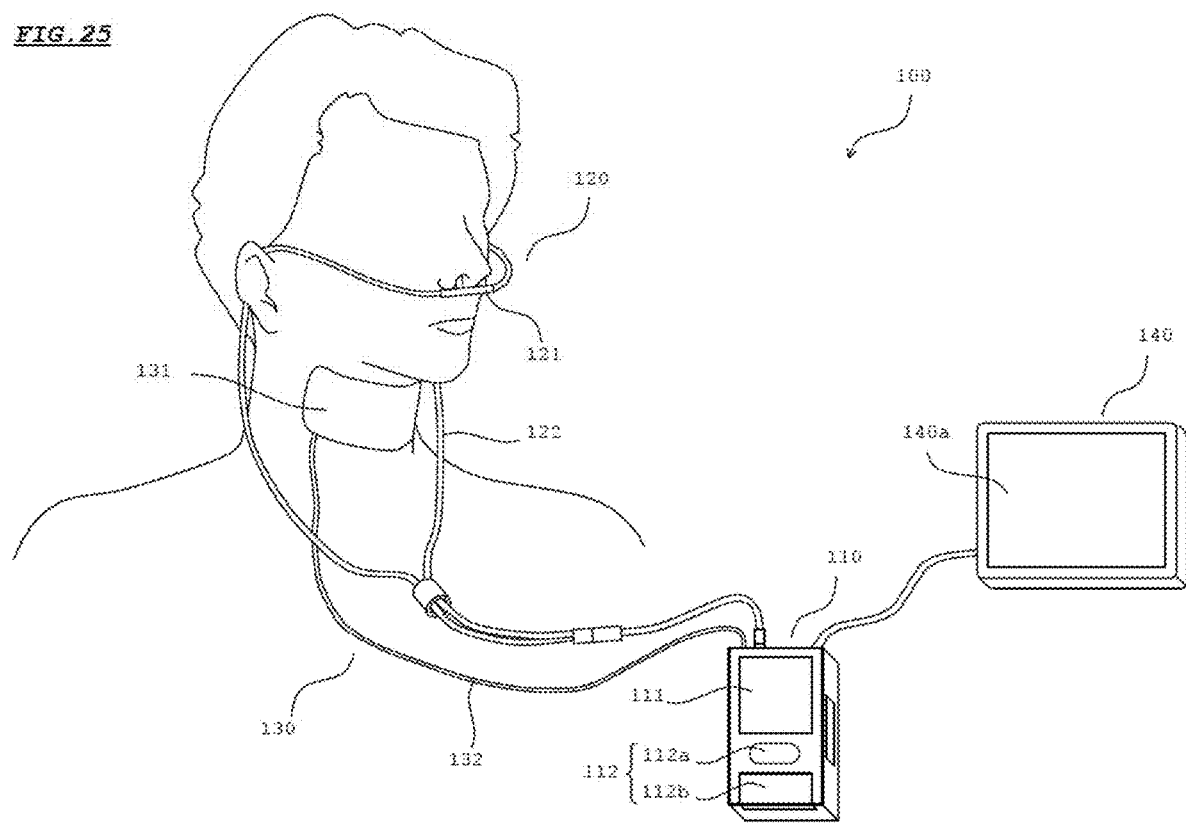
FIG. 25 is an external view showing a configuration of the swallowing diagnosis apparatus according to a modification.

In the embodiment above, the determination in the first swallowing determination part 116b and the determination in the second swallowing determination part 116c are performed in the terminal device 110. However, as shown in FIG. 25, for example, with an external computer 140 such as a tablet computer connected to the terminal device 110, the determination in the first swallowing determination part 116b and the determination in the second swallowing determination part 116c may be performed in the external computer 140.

In this case, the terminal device 110 performs a swallowing estimation process on the basis of respiratory pressure data, biogenic sound data, and larynx displacement data obtained from a patient, and if the terminal device 110 has estimated that swallowing has been performed, the terminal device 110 transmits, to the external computer 140, respiratory pressure data, biogenic sound data, and larynx displacement data extracted in the extraction interval including the swallowing sound generation interval. On the basis of the received data, the external computer 140 performs the determination in the first swallowing determination part 116*b*, and the determination in the second swallowing determination part 116*c*, and displays the determination results on a display 140*a* thereof.

Also in this modification, the effects similar to those in the embodiment above can be exhibited. In this modification, the swallowing diagnosis apparatus 100 is configured by the terminal device 110, the nasal cannula 120, the detection part 130, and the external computer 140.

The external computer 140 may have the functions of the first swallowing determination part 116*b* and the second swallowing determination part 116*c* and the function of the swallowing estimation part 116*a*. In this case, the terminal device 110 continuously transmits, to the external computer 140, respiratory pressure data, biogenic sound data, and larynx displacement data obtained from the patient, and the external computer 140 performs the swallowing diagnosis process shown in FIG. 5B to FIG. 7.

In the embodiment above, the determination in the second swallowing determination part 116*c* is performed, using a combination of feature parameter values based on respiratory pressure data, biogenic sound data, and larynx displacement data. However, the feature parameter value to be used in the determination in the second swallowing determination part 116*c* is not limited thereto. For example, the determination in the second swallowing determination part 116*c* may be performed, using a combination of the feature parameter values based on respiratory pressure data and biogenic sound data among the feature parameter values based on respiratory pressure data, biogenic sound data, and larynx displacement data. Alternatively, the determination in the second swallowing determination part 116*c* may be performed, using a combination of other feature parameter values. Still alternatively, the determination in the second swallowing determination part 116*c* may be performed, using any one of the feature parameter values based on respiratory pressure data, biogenic sound data, and larynx displacement data.

However, as shown in Examination 2 above, when the feature parameter value based on biogenic sound data is used, the determination accuracy in the second swallowing determination part 116*c* becomes highest. Therefore, in the determination in the second swallowing determination part 116*c*, it is preferable to preferentially use the feature parameter value based on biogenic sound data. When the feature parameter value based on respiratory pressure data is used, the determination accuracy in the second swallowing determination part 116*c* becomes second highest. Therefore, when a combination of feature parameter values is used in the determination in the second swallowing determination part 116*c*, it is preferable to use a combination of the feature parameter value based on biogenic sound data and the feature parameter value based on respiratory pressure data.

In the embodiment above, the nasal cannula 120 is used for detection of respiration, but respiration detection means other than the nasal cannula 120 may be used. For example, respiration of the patient may be detected, using a detection band that can detect expansion and contraction of the chest circumference.

In the embodiment above, respiratory pressure data, biogenic sound data, and larynx displacement data are processed in real time, and the estimation by the swallowing estimation part 116*a*, and the determinations by the first swallowing determination part 116*b* and the second swallowing determination part 116*c* are performed. However, a configuration may be employed in which: during a swallowing diagnosis, respiratory pressure data, biogenic sound data, and larynx displacement data are stored in the storage part 117; and after the diagnosis, in accordance with an input of an instruction from the doctor or the like, the swallowing estimation part 116*a*, the first swallowing determination part 116*b*, and the second swallowing determination part 116*c* read out the respiratory pressure data, the biogenic sound data, and the larynx displacement data from the storage part 117, and perform swallowing estimation and determination on the aspiration risk and the possibility of dysphagia.

In addition, the configuration of the display screen for the determination results obtained by the first swallowing determination part 116*b* and the second swallowing determination part 116*c* is not limited to that shown in FIG. 23A, and another screen configuration may be used as appropriate.

The swallowing diagnosis apparatus according to the present invention has an excellent swallowing diagnosis function, and can be used in the field of medical devices.

What is claimed is:

1. A swallowing diagnosis apparatus comprising:
   a sound detection part comprising a sound sensor;
   a respiration detection part comprising a respiration sensor; and
   a controller,
   the controller being configured to perform:
   a swallowing estimation process of estimating that swallowing has occurred, on the basis of matching realized between a biogenic sound generation interval for which a feature quantity satisfying a swallowing estimation condition has been obtained in sound information outputted from the sound detection part, and an apneic interval for which respiration has not been detected for longer than or equal to a predetermined time in respiration information outputted from the respiration detection part;
   a first swallowing determination process of
   detecting, from the respiration information, respiratory phases before and after a period in which swallowing has been estimated as having occurred by the swallowing estimation process, and
   determining whether or not there is an aspiration risk in the swallowing on the basis of the detected respiratory phases;
   a second swallowing determination process of
   extracting reference information including at least one of the sound information and the respiration information in a predetermined period including the period in which swallowing has been estimated as having occurred by the swallowing estimation process,
   obtaining a feature quantity from the extracted reference information, and
   performing a machine learning process on the obtained feature quantity to determine whether or not there is a possibility of dysphagia in the swallowing;
   a display control process of causing a display to display, in a contrastable manner, a determination result obtained by the first swallowing determination process and a determination result obtained by the second swallowing determination process with respect to an identical period in which swallowing has been estimated as having occurred by the swallowing estimation process,
   the controller is configured to, in the second swallowing determination process, extract the sound information as the reference information, obtain the feature quantity from the extracted sound information, and perform a machine learning process on the obtained feature quantity to determine whether or not there is a possibility of dysphagia in the swallowing, and the controller is further configured to, in the second swallowing determination process, extract the respiration information as the reference information, obtain a feature quantity from the extracted respiration information, and perform a machine learning process on the feature quantity obtained from the respiration information and the feature quantity obtained from the sound information, to determine whether or not there is a possibility of dysphagia in the swallowing.

2. The swallowing diagnosis apparatus according to claim 1, further comprising a displacement detection part comprising a displacement sensor, wherein the controller is further configured to, in the second swallowing determination process, extract, as the reference information, displacement information outputted from the displacement detection part in the predetermined period including the period in which swallowing has been estimated as having occurred, obtain a feature quantity from the extracted displacement information, and perform a machine learning process on the feature quantity obtained from the displacement information and the feature quantities respectively obtained from the sound information and the respiration information, to determine whether or not there is a possibility of dysphagia in the swallowing.

3. The swallowing diagnosis apparatus according to claim 2, wherein the controller is configured to, in the swallowing estimation process, estimate that swallowing has occurred when the biogenic sound generation interval and the apneic interval match each other and an amplitude of the displacement information exceeds a predetermined threshold in the biogenic sound generation interval.

4. The swallowing diagnosis apparatus according to claim 1, wherein the controller is configured to, in the second swallowing determination process, subject the reference information to Fourier transform to obtain a frequency spectrum, apply linear predictive coding to the obtained frequency spectrum to obtain a spectrum envelope, and sample the obtained spectrum envelope at a predetermined frequency interval, thereby obtaining the feature quantity.

5. The swallowing diagnosis apparatus according to claim 4, wherein the controller is configured to, in the second swallowing determination process, divide the frequency spectrum for each predetermined frequency band, apply linear predictive coding for each frequency band to obtain a spectrum envelope, sample the obtained spectrum envelope of each frequency band at a predetermined frequency interval, thereby obtaining the feature quantity.

6. The swallowing diagnosis apparatus according to claim 1, wherein the controller is configured to, in the second swallowing determination process, subject the reference information to Fourier transform to obtain a frequency spectrum, apply linear predictive coding to the obtained frequency spectrum to obtain a coefficient at each order in the linear predictive coding, and obtain a group of the obtained coefficients, as the feature quantity.

7. The swallowing diagnosis apparatus according to claim 1, wherein the machine learning process is a support vector machine.

8. A swallowing diagnosis apparatus comprising:

a sound detection part comprising a sound sensor;

a respiration detection part comprising a respiration sensor; and a controller, the controller being configured to perform:

a swallowing estimation process of estimating that swallowing has occurred, on the basis of matching realized between a biogenic sound generation interval for which a feature quantity satisfying a swallowing estimation condition has been obtained in sound information outputted from the sound detection part, and an apneic interval for which respiration has not been detected for longer than or equal to a predetermined time in respiration information outputted from the respiration detection part; and a swallowing determination process of extracting reference information including at least one of the sound information and the respiration information in a predetermined period including a period in which swallowing has been estimated as having occurred by the swallowing estimation process, subjecting the extracted reference information to Fourier transform to obtain a frequency spectrum, applying linear predictive coding to the obtained frequency spectrum to obtain a spectrum envelope, sampling the obtained spectrum envelope at a predetermined frequency interval to obtain a feature quantity, and performing a machine learning process on the obtained feature quantity to determine whether or not there is a possibility of dysphagia in the swallowing.

9. A storage medium having stored therein a program, the program being configured to cause a computer of a swallowing diagnosis apparatus which includes:

a sound detection part comprising a sound sensor, and a respiration detection part comprising a respiration sensor, to perform:

a swallowing estimation function of estimating that swallowing has occurred, on the basis of matching realized between a biogenic sound generation interval for which a feature quantity satisfying a swallowing estimation condition has been obtained in sound information outputted from the sound detection part, and an apneic interval for which respiration has not been detected for longer than or equal to a predetermined time in respiration information outputted from the respiration detection part;

a first swallowing determination function of detecting, from the respiration information, respiratory phases before and after a period in which swallowing has been estimated as having occurred by the swallowing estimation function, and determining whether or not there is an aspiration risk in the swallowing on the basis of the detected respiratory phases;

a second swallowing determination function of extracting reference information including at least one of the sound information and the respiration information in a predetermined period including the period in which swallowing has been estimated as having occurred by the swallowing estimation function, obtaining a feature quantity from the extracted reference information, and performing a machine learning process on the obtained feature quantity to determine whether or not there is a possibility of dysphagia in the swallowing;

a display control function of causing a display to display, in a contrastable manner, a determination result obtained by the first swallowing determination function and a determination result obtained by the second swallowing determination function with respect to an identical period in which swallowing has been estimated as having occurred by the swallowing estimation function, the second swallowing determination function extracts the sound information as the reference information, obtains the feature quantity from the extracted sound information, and performs a machine learning process on the obtained feature quantity to determine whether or not there is a possibility of dysphagia in the swallowing, and the second swallowing determination function further extracts the respiration information as the reference information, obtains a feature quantity from the extracted respiration information, and performs a machine learning process on the feature quantity obtained from the respiration information and the feature quantity obtained from the sound information, to determine whether or not there is a possibility of dysphagia in the swallowing.

10. The storage medium according to claim 9, wherein the swallowing diagnosis apparatus further includes a displacement detection part comprising a displacement sensor, and the second swallowing determination function further extracts, as the reference information, displacement information outputted from the displacement detection part in the predetermined period including the period in which swallowing has been estimated as having occurred; obtains a feature quantity from the extracted displacement information; and performs a machine learning process on the feature quantity obtained from the displacement information and the feature quantities respectively obtained from the sound information and the respiration information, to determine whether or not there is a possibility of dysphagia in the swallowing.

11. The storage medium according to claim 10, wherein when the biogenic sound generation interval and the apneic interval match each other and an amplitude of the displacement information exceeds a predetermined threshold in the biogenic sound generation interval, the swallowing estimation function estimates that swallowing has occurred.

12. The storage medium according to claim 9, wherein the second swallowing determination function subjects the reference information to Fourier transform to obtain a frequency spectrum, applies linear predictive coding to the obtained frequency spectrum to obtain a spectrum envelope, and samples the obtained spectrum envelope at a predetermined frequency interval, thereby obtaining the feature quantity.

13. The storage medium according to claim 12, wherein the second swallowing determination function divides the frequency spectrum for each predetermined frequency band, applies linear predictive coding for each frequency band to obtain a spectrum envelope, and samples the obtained spectrum envelope of each frequency band at a predetermined frequency interval, thereby obtaining the feature quantity.

14. The storage medium according to claim 9, wherein the second swallowing determination function subjects the reference information to Fourier transform to obtain a frequency spectrum, applies linear predictive coding to the obtained frequency spectrum to obtain a coefficient at each order in the linear predictive coding, and obtains a group of the obtained coefficients, as the feature quantity.

15. The storage medium according to claim 9, wherein the machine learning process is a support vector machine.

* * * * *